(12) United States Patent
Stark et al.

(10) Patent No.: US 8,753,601 B2
(45) Date of Patent: Jun. 17, 2014

(54) FLAME SYNTHESIS OF METAL SALT NANOPARTICLES, IN PARTICULAR CALCIUM AND PHOSPHATE COMPRISING NANOPARTICLES

(75) Inventors: Wendelin Jan Stark, Zürich (CH); Sotiris-Emmanuel Pratsinis, Zürich (CH); Marek Maciejewski, Zürich (CH); Stefan Fridolin Loher, Zürich (CH); Alfons Baiker, Opfikon (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 830 days.

(21) Appl. No.: 12/928,185

(22) Filed: Dec. 6, 2010

(65) Prior Publication Data

US 2011/0150737 A1 Jun. 23, 2011

Related U.S. Application Data

(62) Division of application No. 10/592,913, filed as application No. PCT/CH2004/000151 on Mar. 15, 2004, now Pat. No. 7,879,303.

(51) Int. Cl.
| | |
|---|---|
| *C01B 25/10* | (2006.01) |
| *C01B 15/16* | (2006.01) |
| *C01B 25/26* | (2006.01) |
| *C01F 17/00* | (2006.01) |

(52) U.S. Cl.
USPC ........... 423/301; 423/263; 423/277; 423/305; 423/308; 423/311; 423/419.1; 502/304

(58) Field of Classification Search
USPC ................ 423/263, 277, 301, 305, 308, 311, 423/419.1; 502/304
See application file for complete search history.

(56) References Cited

U.S. PATENT DOCUMENTS

| | | | |
|---|---|---|---|
| 3,900,331 A | 8/1975 | Cassidy | |
| 4,501,823 A | 2/1985 | Masuda | |

(Continued)

FOREIGN PATENT DOCUMENTS

| | | |
|---|---|---|
| EP | 0803471 A2 | 10/1997 |
| EP | 0841304 A1 | 5/1998 |

(Continued)

OTHER PUBLICATIONS

Katsuki et al., Microwave-versus conventional-hydrothermal synthesis of hydroxyapatite crystals from Gypsum, J. Am. Ceram. Soc, 82, 8, 2257-2259, 1999.*

(Continued)

*Primary Examiner* — Bijan Ahvazi
(74) *Attorney, Agent, or Firm* — Cooper & Dunham LLP

(57) ABSTRACT

Described is a method for the production of metal salts, wherein the cationic metal is preferably selected from Group I to IV metals and mixtures thereof and the anionic group is selected from phosphates, silicates, sulfates, carbonates, hydroxides, fluorides and mixtures thereof, and wherein said method comprises forming a mixture of at least one metal source that is a metal carboxylate with a mean carbon value per carboxylate group of at least 3 and at least one anion source into droplets and oxiding said droplets in a high temperature environment, preferably a flame. This method is especially suited for the production of calcium phosphate biomaterials such as hydroxyapatite (HAp,Ca10(PO4)6(OH)2) and tricalcium phosphate (TCP,Ca3(PO4)2) that exhibit excellent biocompatibility and osteoconductivity and therefore are widely used for reparation of bony or periodontal defects, coating of metallic implants and bone space fillers.

15 Claims, 17 Drawing Sheets

(56) References Cited

U.S. PATENT DOCUMENTS

| | | | |
|---|---|---|---|
| 4,659,617 A | 4/1987 | Fujii et al. | |
| 4,711,769 A | 12/1987 | Inoue et al. | |
| 4,772,736 A | 9/1988 | Edwards et al. | |
| 4,855,118 A * | 8/1989 | Ichinose et al. | 423/301 |
| 5,276,251 A | 1/1994 | Kamei et al. | |
| 5,395,606 A | 3/1995 | Xiao et al. | |
| 5,514,822 A | 5/1996 | Scott et al. | |
| 5,958,361 A | 9/1999 | Laine et al. | |
| 5,984,997 A | 11/1999 | Bickmore et al. | |
| 5,989,514 A | 11/1999 | Bi et al. | |
| 6,013,318 A | 1/2000 | Hunt et al. | |
| 6,030,914 A | 2/2000 | Matsui | |
| 6,887,566 B1 | 5/2005 | Hung et al. | |
| 7,211,236 B2 | 5/2007 | Stark et al. | |
| 7,220,398 B2 | 5/2007 | Sutorik et al. | |
| 7,229,600 B2 | 6/2007 | Yadav | |
| 2003/0101659 A1 | 6/2003 | Katusic et al. | |
| 2003/0235624 A1 | 12/2003 | Mangold et al. | |
| 2004/0050207 A1 | 3/2004 | Wooldridge et al. | |
| 2004/0126298 A1 | 7/2004 | Stark et al. | |
| 2005/0227864 A1 | 10/2005 | Sutorik et al. | |
| 2006/0229197 A1 | 10/2006 | Stark et al. | |

FOREIGN PATENT DOCUMENTS

| | | |
|---|---|---|
| EP | 1142830 A1 | 10/2001 |
| EP | 1 378 489 | 1/2004 |
| JP | 2001-146584 | 6/1997 |
| JP | 2001-039716 | 2/2001 |
| JP | 2001-287152 | 10/2001 |
| JP | 2003-139869 | 5/2003 |
| WO | WO 00-27754 | 5/2000 |
| WO | WO 01-36332 | 5/2001 |
| WO | WO 03-070640 | 8/2003 |
| WO | WO 2004/103900 | 12/2004 |
| WO | WO 2005/087660 | 9/2005 |

OTHER PUBLICATIONS

Kwon et al. Synthesis and dissolution behavior of β-TCP and HA/β-TCP composite powders, Journal of the European Ceramic Society, 23, 1039-1045, 2003.*
L. Madler et al. (2002) "Flame-made ceria nanoparticles", J. Mater, Res., vol. 17, No. 6, pp. 1356-1362.
A.R. DiGiampaolo et al. (1998) "ZrO2 coatings on stainless steal by aerosol thermal spraying", Advances in Tech. Materials & Mat. Processing Journal, 1(1), 90-100 (abstract).
L. Madler et al. (2002) "Bismuth Oxide Nanoparticles by Flame Spray Pyrolysis", J. Am. Ceram. Soc., vol. 85, No. 7, pp. 1713-1718.
S.T. Aruna et al. (1998) "Combustion Synthesis and Properties of Nanostructured Ceria—Zirconia Solid Solutions", Nanostructured Materials, vol. 10, No. 6, pp. 995-964.
U.S. Appl. No. 10/592,913, filed Nov. 13, 2006.
Madler et al. (Feb. 2002) "Controlled synthesis of nanostructured particles by flame spray pyrolysis" Journal of Aerosol Science, vol. 33, pp. 369-389.
Pratsinis, Sotiris E. (1998) "Flame Aerosol Synthesis of Ceramic Powders," Prog. Energy Combust. Sci. vol. 24, pp. 197-219.
Shoichi Fujiwara et al., Chem. Abs. Ser., Columbus, OH, US; "Preparation of superconducting YBCO thick films by spray-pryolysis of organic acid salts" Jun. 13, 1992, XP002264388.
W. J. Stark et al., (2003) Chem. Comm. "Flame synthesis of nanocyrstalline ceria—zirconia: effect of carrier liquid", No. 5, Feb. 20, 2003, pp. 588-589, XP002264387.
Jarcho, M. (1981) "Calcium—Phosphate Ceramics as Hard Tissue Prosthetics." Clin. Orthapaedics and Related Research, 259-278.
de Groot, K. (1983) "Bioceramics of Calcium Phosphate" (ed. de Groot, K.) (CRC Press, Boca Raton).
LeGeros, R. Z. (1991) "Calcium Phosphates in Oral Biology and Medicine" (ed. LeGeros, R.Z.) (S. Karger, Basel).
Metsger, D.S. et al. (1982) "Tricalcium Phosphate Ceramic—a Resorbable Bone Implant—Review and Current Status", Journal of the Am. Dental Assoc. 105, 1035-1038.

LeGeros, R. Z. et al. (1995) "Encyclopedic Handbook of Biomaterials and Bioengineering" eds. Wise, D.L., J., T.D., & E., A.D., (Marcel Dekker, New York).
Dong, Z. L. et al. (2003) "TEM and STEM analysis on heat-treated and in vitro plasma-sprayed hydroxyapatite/Ti-6A1-4V composite coatings" Biomaterials 24, 97-105.
Cleries, L. et al. (1998) "Dissolution behaviour of calcium phosphate coatings obtained by laser ablation" Biomaterials 19, 1483-1487.
Arias, J. L. et al. (2003) "Micro- and nano-testing of calcium phosphate coatings produced by pulsed laser deposition." Biomaterials 24, 3403-3408.
Tadic, D. et al. (2002) "Continuous synthesis of amorphous carbonated apatites" Biomaterials 23, 2553-2559.
Sarkar, M. R. et al. (2001) "First histological observations . . . a novel calcium phosphate bone substitute material in human cancellous bone" Jour. of Bio. Mat. Res. 58, 329-334.
Overgaard, S. et al. (1999) "The influence of cyrstallinity of the hydroxyapatite coating on the fixation of implants . . . " Jour. of Bone & Joint Surg.—Brit. vol. 81B, 725-731.
Knaack, D. et al. (1998) "Resorbable calcium phosphate bone substitute" Journal of Biomedical Materials Research, 43, 399-409.
Stark, W. J. et al. (2002) "Flame-made titania/silica epoxidation catalysts: Toward large-scale production" Indus. & Engin. Chem. Res. 41, 4921-4927.
Ravaglioli, A. & Krajewski, A. (1992) "Bioceramics: Materials, Properties, Applications" p. 432, Chapman & Hall, London.
Gauthier, O. et al. (1998) "Macroporous biphasic calcium phosphate ceramics: influence of macropore diameter & macroporosity percentage on bone ingrowth" Biomat. 19, 133-139.
Weiss, P. et al. (2003) "Synchrotron X-ray microtomogrophy . . . provides 3-D imaging representation of bone ingrowth in calcium phosphate biomaterials" Biomat. 24, 4591-4601.
Yuan, H. P. et al. (1998) "Osteoinduction by calcium phosphate biomaterials" Journal of Materials Science-Materials in Medicine 9, 723-726.
Bignon, A. et al. (2003) "Effect of micro & macroporosity of bone substitutes on their mechanical properties & cellular response" Jou. of Mat. Sci-Mat. in Med. 14, 1089-1097.
Yuan, H. P. et al. (2001) "Bone formation induced by calcium . . . in soft tissue of dogs: a cpmarative study b/w porous alpha-TCP & beta-TCP" Jou of Mat. Sci-Mat in Med. 12, 7-13.
Yuan, H. P. et al. (2002) "A comparison of the osteoinductive potential of 2 calcium phosph. ceramics implanted intramusc. in goats" Jou. of Mat. Sci-Mat in Med. 13, 1271-1275.
Yuan, H. P. et al. (2000) "Tissue responses of calcium phosphate cement: a study in dogs" Biomaterials 21, 1283-1290.
Yuan, H. P. et al. (1999) "A preliminary study on osteoinduction of two kinds of calcium phosphate ceramics" Biomaterials 20, 1799-1806.
Somrani, S. et al. (2003) "Thermal evolution of amorphous tricalcium phosphate" Journal of Materials Chemistry 13, 888-892.
Peters, F. et at (2000) "The structure of bone studied with synchrotron X-ray diffraction, X-ray absorption spectorscopy and thermal analysis" Thermachimica Acta 361, 131-138.
Suchanek, W. et al (2002) "Mechanochemical-hydrothermal synthesis of carbonated apattie powders at room temprature" Biomaterials 23, 699-710.
Baxter, J. D. et al. (1966) "Physical State of Bone Carbonate—a Comparative Infra-Red Study in Several Mineralized Tissues" Yale Journal of Biology & Medicine 38, 456.
Emerson, W. H. et al. (1962) "The Infra-Red Absorption Spectra of Carbonate in Calcified Tissues" Archives of Oral Biology 7, 671-683.
Fowler, B. O. "Infrared Studies of Apatites .1. Vibrational Assignment for Calcium, Strontium & Barium Hydroxyapatites Utilizing Isotopic Substitution" Inorg.Chem. 13, 194-207.
Jillavenkatesa, A. et al. (1998) "The infrared & Raman spectra of beta and alpha-tricalcium phosphate (Ca-3(PO4)(2))" Spectroscopy Letters 31, 1619-1634.
Dorozhkin, S. V. et al. (2002) "Biological & medical significance of calcium phosphates" Angewandte Chemie-International Edition 41, 3130-3146.

(56) References Cited

OTHER PUBLICATIONS

Daculsi, G. et al (1997) "International Review of Cytology—a Survey of Cell Biology" vol. 172, 129-191, Academic Press Inc, San Diego.
Fulmer, M. T. et al. (2002) "Measurements of solubilities and dissolution rates of several hydroxyapatites" Biomaterials 23, 751-755.
Nelson, D. G. A. (1981) "The Influence of Carbonate on the Atomic-Structure and Reactivity of Hydroxyapatite" Journal of Dental Research 60, 1621-1629.
Cornilsen, B. C. et al. (1979) "Vibrational-Spectra of Beta-Ca2p2o7 and Gamma-Ca2p2o7" Journal of Inorganic & Nuclear Chemistry 41, 602-605.
Dewaal, D. et al. (1994) "Vibrational-Spectra of a Solid-Solution of Cadmium and Calcium Pyrophosphate" Materials Research Bulletin 29, 1129-1135.
Hezel, A. et al. (1967) "Vibrational Spectra of Some Divalent Metal Pyrophsophates" SPectrochimica Acta Part a—Molecular Spectroscopy A 23, 1583.
Pena, J. et al. (2003) "Hydroxyapatite, tricalcium phosphate and biphasic materials prepared by a liquid mix technique" Journal of the European Ceramic Society 23, 1687-1696.
Rigby, S. P. et al. (2004) "Characterisation of porous solids using integrated nitrogen sorption and mercury porosimetry" Chemical Engineering Science 59(1): 41-51.
W. J. Stark, et al. (2002) Aerosol flame reactors for manufacture of nanoparticles. Powder Technol., 126, 103-108.
English language translation of Jun. 17, 2010 Official Action issued in Japanese Patent Application No. 2007-503170.
Japanese Patent Application Publication No. 62-256707, published Nov. 9, 1987, including Abstract in English and partial translation of the specification.
Laine, R. M., et al. (2000) "Low Cost Nanopowders for Phosphor and Laser Applications by Flame Spray Pyrolysis", J. Metastable 5 Nanocryst. Mat., 2000, 8, 500.
Laine, R. M., et al. (1999) "Making nanosized oxide powders from precursors by flame spray pyrolysis", Key. Eng. Mat., 1999, 159, 17.
Yoshioka, T., et al. (1992) "Preparation of spherical ceria-doped tetragonal zirconia by the spray pyrolysis method", J. Mater. Sci. Lett., 1992, 11, 51.
Oljaca, M., et al. (2002) "Flame Synthesis of nanopowders 20 via combustion chemical vapor deposition", J. Mater. Sci. Lett., 21, 621-626.
Maric, R., et al. (2003) "Electrolyte Materials for Intermediate Temperature Fuel Cells Produced via Combustion . . . ", Electrochemical and Solid State Letters, 6 (5) A 91.
T. Tani, et al. (2002) "Synthesis of zinc oxide/silica composite nanoparticles by flame spray pyrolysis", Journal of Materials Science, vol. 32:4627-4632.
Takao Tani, et al. (2002) "Homogeneous ZnO nanoparticles by flame spray pyrolysis", Journal of Nanoparticale Research, vol. 4:337-343.
International Preliminary Report on Patentability for International Application No. PCT/CH04/000151, issued Sep. 19, 2006.
Jan. 5, 2006 Office Action issued from the U.S. Patent and Trademark Office in connection with U.S. Appl. No. 10/602,305.
Feb. 22, 2006 Office Action issued from the U.S. Patent and Trademark Office in connection with U.S. Appl. No. 10/602,305.
Sep. 15, 2006 Notice of Allowability issued from the U.S. Patent and Trademark Office in connection with U.S. Appl. No. 10/602,305.
Jan. 31, 2007 Notice of Allowability issued from the U.S. Patent and Trademark Office in connection with U.S. Appl. No. 10/602,305.
Jul. 24, 2008 Office Action issued from the U.S. Patent and Trademark Office in connection with U.S. Appl. No. 10/557,399.
Feb. 25, 2009 Office Action issued from the U.S. Patent and Trademark Office in connection with U.S. Appl. No. 10/557,399.
Aug. 5, 2009 Office Action issued from the U.S. Patent and Trademark Office in connection with U.S. Appl. No. 10/557,399.
Jan. 19, 2010 Office Action issued from the U.S. Patent and Trademark Office in connection with U.S. Appl. No. 10/557,399.
German language translation of May 13, 2009 Official Action issued in a counterpart Japanese application in connection with U.S. Appl. No. 10/557,399.
German language translation of Dec. 11, 2009 Official Action issued in a counterpart Japanese application in connection with U.S. Appl. No. 10/557,399.

* cited by examiner

Figur 2A

FLAME SYNTHESIS OF METAL SALT NANOPARTICLES, IN PARTICULAR CALCIUM AND PHOSPHATE COMPRISING NANOPARTICLES

This application is a divisional of U.S. Ser. No. 10/592,913, filed Nov. 13, 2006, now U.S. Pat. No. 7,879,303, which is a §371 national stage of PCT/CH04/00151, filed Mar. 15, 2004, the contents of all of which are hereby incorporated by reference.

TECHNICAL FIELD

This application relates to fine metal salt particles and a method for producing same by means of flame spray pyrolysis, in particular calcium and phosphate containing particles.

BACKGROUND ART

Flame spray pyrolysis[13] currently established itself as a suitable method for the preparation of nano-particles, most notably, oxides containing main group and transition metals[41]. It has rapidly evolved into a scalable process to oxide nanoparticles for catalyst preparation[14,15] and industrial-scale flame-aerosol synthesis today produces megaton quantities of carbon, silica and titania. Experimentally, the flame spray reactors consist of a capillary surrounded by a narrow adjustable orifice (see FIG. 1). The precursor liquid is dispersed at the tip resulting in a well-defined spray. The surrounding methane/oxygen supporting flame ignites the spray and the flame converts the precursor to the corresponding materials.

For many applications nanoparticulate materials are desired. Such materials comprise calcium phosphates such as tricalciumphosphates but also apatites. Calcium phosphate biomaterials have attracted a tremendous interest in clinical medicine. Both hydroxyapatite (HAp or OHAp, $Ca_{10}(PO_4)_6(OH)_2$) and tricalcium phosphate (TCP, $Ca_3(PO_4)_2$) exhibit excellent biocompatibility and osteoconductivity[1,2]. They are widely used for reparation of bony or periodontal defects, coating of metallic implants and bone space fillers. However, traditional methods (precipitation, sol-gel synthesis, hydrothermal method or solid-state reactions)[1,3-5] suffer from a limited range of accessible materials and morphology. Wet-phase preparation generally requires time and cost intensive post treatments such as washing and drying. Solid-state reaction involves prolonged sintering and therefore results in low specific surface area powder. The rather dense materials display a lack of microporosity, reduce contact to the body fluid and hinder resorption in vivo.

Recently reported preparation methods comprise, plasma spraying6 and pulsed laser deposition[7,8]. They have resulted in advantageous coatings on implant surfaces. Moreover, amorphous calcium phosphates have shown to result in improved resorption properties[9-11] and are promising materials for self-setting cements[12] making them a most valuable target.

All these methods, however, have several drawbacks. They either lead to mixtures that can not be separated or only with considerable effort, and/or they lead to a too dense material, and/or they cannot be applied for bulk synthesis, and/or they are not usable in large scale production. Thus there is still a need for an improved production method allowing the production of pure materials, preferably also in large scale production, and an improved material obtainable by such method.

DISCLOSURE OF THE INVENTION

Hence, it is a general object of the invention to provide a method for the production of metal salts, wherein the anionic group is selected from phosphates, borates, silicates, sulfates, carbonates, hydroxides, fluorides and mixtures thereof, in particular nanoparticulate metal salts, preferably metal salts wherein the metal is selected from groups I, II, III, IV metals, the 3d transition metals, the lanthanoids (rare earth group) predominantly occurring in oxidation states II and III, but optionally also in oxidation state I or IV, and mixtures of the mentioned metals. Since all the above mentioned metals usually have oxidation states I to IV, they are further on considered to be encompassed by the term "group I to IV metals". Other metals can be present depending on the type of salt and area of application. In some cases, doped salts or mixtures or different salts are preferred.

Another object of the present invention was to provide nanoparticulate, optionally percolating metal salts.

Yet another object of the present invention was to provide uses for such metal salts.

Now, in order to implement these and still further objects of the invention, which will become more readily apparent as the description proceeds, the method is manifested by the features that a mixture of at least one metal source that is a metal carboxylate with a mean carbon value per carboxylate group of at least 3 and at least one anion source is formed into droplets and that said droplets are oxidized in a high temperature environment.

In preferred metal salts the metal comprises calcium. Much preferred are metal salts with a high calcium content of at least 80 atom-% calcium (sum of all cations is 100 atom-%), preferably at least 90%, most preferably at least 95%.

The sum of cationic metals may comprise further Group I-IV metals, preferably metals selected from the group consisting of sodium, potassium, magnesium, zinc, strontium and barium, rare earth metals, in particular gadolinium, and mixtures of two or more of said metals.

Preferably the sum of anionic groups comprises anionic groups selected from phosphates, sulfates, borates, hydroxides, carbonates, fluorides and mixtures thereof in amounts of at least 80 mole-% of the theoretically calculated necessary amount of anions if electron neutrality in the salt is assumed, preferably at least 90%, more preferred at least 95%. Most preferred are pure materials wherein more than 98% or even 99% of all negative charges in the salt are covered by one of the above anions. In much preferred compounds at least part of the anionic groups are phosphates, whereby compounds with a metal:phosphate molar ratio of 3:1 (e.g. $Na_3PO_4$) to 1:1 (e.g. $AlPO_4$, enamel) are preferred.

The method of the present invention is especially suited to produce a metal salt selected from the group consisting of amorphous tricalciumphosphate, alpha-tricalciumphosphate, beta-tricalciumphosphate, apatites and mixtures thereof.

Preferred apatites that are producible by the above method in high purity have the formula $Ca_{10}(PO_4)_6(OH)_{2x}F_{2y}(CO_3)_z$ whereby x, y and z each range from 0 to 1 and the sum of x+y+Z is 1. Although z can vary from 0 to 1, dependent on the application specific ranges may be preferred. For e.g. medical applications, carbonate can be advantageous. The carbonate content in apatites can e.g. be 3-8 wt % carbonate measured by thermographimetric analysis. The $CO_2$ detection can be done by a differential scanning calorimeter coupled to a mass spectrometer.

The method of the present invention has been found suitable for the production of very pure products, such as phase pure amorphous tricalciumphosphate, alpha-tricalciumphosphate or beta-tricalciumphosphate, or tricalciumposphate poor or even tricalciumposphate free apatites. The purity of the compound formed that can be achieved is in the range of at least 96% by weight, preferably at least 98% by weight, most preferred at least 99% by weight. Preferred products that can be obtained in high purity comprise amorphous tricalciumphosphate, alpha-tricalciumphosphate or beta-tricalciumphosphate or hydroxyapatite or fluorapatite or hydroxyfluorapatite.

As mentioned above, the metal source is a metal carboxylate with a mean carbon value per carboxylate group of at least 3, preferably at least 4, much preferably at least 5, and most preferred between 5 and 8. Preferably, the metal carboxylate is selected from the group consisting of C1 to C18 carboxylates and mixtures thereof, more preferably C4 to C12 carboxylates and mixtures thereof, much preferably C5 to C8 carboxylates and mixtures thereof, in particular octoates such as 2-ethylhexanoic acid salts.

The metal carboxylate(s) and the one or more anion source(s), i.e. the phosphate and/or one or more other anion(s) or anions precursor(s) comprising droplets are preferably oxidized in a flame.

Prior to being formed into droplets, the metal carboxylate usually has a viscosity of at most 100 mPas, preferably at most 40 mPas, more preferably at most 20 mPas. If the metal carboxylate does not have such viscosity, such viscosity may be obtained by heating and/or by providing a mix of the at least one metal carboxylate and at least one viscosity reducing solvent.

Suitable viscosity reducing solvents may comprise one or more acids. While viscosity reducing solvents may consist of one or more acids, often 50% w/w total acid(s) or less may be used and in some cases acids are neither needed nor desired. Preferred acids are C1 to C10 carboxylic acids.

The solvent may comprise at least one low molecular weight and/or low viscosity apolar solvent, in particular an aromatic or aliphatic, unsubstituted, linear or branched hydrocarbon, preferably a solvent selected from the group consisting of toluene, xylene, lower aliphatic hydrocarbons and mixtures thereof.

The anion source is selected in view of sufficient solubility in the above defined solvent. Suitable anion sources comprise a phosphate source selected from inorganic phosphorous compounds and/or organophosphorous compounds soluble in solvents or solvent mixtures having a combustion enthalpy of at least 13 kJ/g, preferably at least 22.5 kJ/g, most preferred at least 25.5 kJ/g, in particular phosphoric acid and/or organic esters of phosphoric acid and/or phosphines, in particular phosphorous compounds constituting solvents or leading to solvent mixtures with the above-mentioned properties, and/or a fluoride source being a fluoride derivative of an organic compound, said fluoride derivative being soluble in the above defined solvent or solvent mixture, in particular trifluoroacetic acid, and/or a silicate source selected from organic silicates and/or organosilicon compounds soluble in the above defined solvent or solvent mixture, in particular tetraethyl silicate, and/or a sulfate source selected from organic sulfur containing compounds and/or sulfuric acid said sulfate source being soluble in the above defined solvent or solvent mixture, in particular dimethyl sulfoxide (DMSO)

a carbonate source selected from any organic carbon source, such as hydrocarbons, carboxylic acids, alcohols, metal carboxylates and mixtures thereof.

If metal carbonates shall be produced, the metal carboxylate used as metal source can simultaneously act as anion source, whereby the cool-down process (residence time of the particle containing off-gas at specific temperatures) is relevant for the purity.

Suitable apparatus for performing the flame oxidation are spray burners[42,43], or in particular oil burners.

Usually the oxidation is performed at a temperature of at least 600° C., preferably at least 800° C., more preferably at least 1000° C. and most preferably in a range of 1200 to 2600° C., in particular at about 1600° C.

A suitable method for preparing the metal carboxylate starts from a metal oxide, a metal hydroxide, a metal carbonate, a metal halide, such as a chloride or bromide, or a metal lower alkyl oxide, in particular a C1 to C4 alkyl oxide. For good results the enthalpy of the metal carboxylate or the metal carboxylate comprising solution should be at least 13 kJ/g, preferably at least 18 kJ/g, more preferred at least 22.5 kJ/g and most preferred at least 25.5 kJ/g.

It is possible to get a high production rate if the solution comprises metal carboxylate(s) in an amount corresponding to at least 0.15 moles metal per liter, and anion source(s) in an amount corresponding to at least 0.05 moles anionic groups per liter. It is, however, also possible to make the solution up to 10 times more concentrated, whereby concentrations of about 0.8 to 2 moles metal and corresponding amounts of anionic groups/anion precursors are presently preferred. Since the conversion of the metal source to the metal salt is almost free of any loss, a high production rate, only dependent on the solubility of the starting materials, the viscosity of the solution to be sprayed and the nozzle/burner capacity is obtained. By adding at least 1 anionic group per 3 metal atoms/ions, the conversion to a metal salt of the present invention and not a metal oxide is achieved.

In order to bring the nanoparticle manufacture from the pilot-scale production to an industrial scale synthesis (kg to ton quantities), some additional problems are to be faced. The most prominent is the choice of readily accessible metal precursors that allow sufficiently high production rates. The present invention links the manufacture of nanoparticles to specific metal containing products and anion sources, as well as optionally specific solvents. Besides of the specific selection of starting materials, production rate is also influenced by the burner. Using multiple arrays as described in WO 02/061163 entails problems with maintenance, nozzle clogging, space, reproducibility and others. Thus it is much preferred to use few burners to make the same quantity of powder, preferably common oil burners. Oil burners with well above 100 kg oil/h are available and thus they are well suited for high production rates. As it will become apparent within this invention, such a burner can (without any scale-up) achieve amounts of 8 kg $Ca_3(PO_4)_2$ or 9 kg hydroxyapatite particles per hour (for 100 kg feed/hour). with scale-up amounts of about 12 or 13 kg, respectively, are expected. Commercially available oil-burners suitable to convert the here described liquid into corresponding metal salts are—to only mention a few—available from Vescal AG, Heizsysteme, Industries-trasse 461, CH-4703 Kestenholz under the designation of OEN-151LEV, or OEN-143LEV, or OEN-331LZ to OEN-334LZ.

The method of the present invention can also be applied for the production of substoichiometric metal salts. In such production the flame comprises insufficient oxygen for full combustion or conversion of the reactants. Thus, substoichiometric means that e.g. a metal is present in different oxidation states.

The metal salt as-prepared (as-prepared designates a product directly after high temperature production, in particular directly after the burner/flame) may comprise some carbonate. In case that less or no carbonate is desired, a heat treatment, optionally in the presence of humidity may be performed. In the case of apatite such treatment allows to reduce the $CO_2$ content to close to zero. Suitably such treatment is performed at temperatures of from 500° C. to 900° C. and a water partial pressure of 0.1 to 100 mbar.

Dependent on the $CO_2$ removal conditions, this step may simultaneously act as tempering/sintering procedure, or a separate tempering/sintering procedure may be provided. By such temperature treatment, the crystal structure may be influenced and/or a percolating product with specific features may be obtained. Suitable sintering methods can be found by applying the analytical methods described below in connection with calcium phosphate (Ca/P) samples. Such methods comprise mercury porosimetry and nitrogen adsorption (BET) such as outlined in Rigby et al. (2004)[40] for determining the specific surface area and pore size and pore structure analysis. Further methods are transmission electron microscopy (TEM) and scanning electron microscopy (SEM) for morphological studies, Fourier transform infrared (FTIR) spectroscopy and X-ray diffraction for product characterization, as well as differential thermal analysis (DTA) for monitoring temperature dependent changes.

A further aspect of the present invention is a metal salt, in particular a metal salt obtainable by the above described method.

Metal salts of the present invention comprise the following features:

They have a BET equivalent diameter as-prepared in the range of 5 to 200 nm, preferably of about 20 nm. In specific cases, larger than 20 nm diameters such as 50 nm or 100 nm are obtained, especially if the melting point of the corresponding salt is below 1000° C.

Furthermore, the salts of the present invention are characterized in that they usually do not release more than 7.5 wt % water upon heating to 900° C. at a heating rate of 10° C. per minute. Preferably, they have less than 5 wt % water release, most preferred less than 4.5 wt % water release.

The salts of the present invention usually release more than 90 wt % of all water upon heating to 500° C. at a heating rate of 10° C. per minute. Preferably, upon heating to 400° C., most preferably upon heating to 350° C. The water release curve (see e.g. FIG. 5) supports the assumption that water is only present adsorbed on the surface.

The water release criteria markedly distinguish the material of the present invention from wet phase material. Such material slowly releases water in a large temperature range of several hundreds ° C. The release curve of wet phase product supports the assumption that water is incorporated within the crystal lattice such that it is kept much stronger.

Dependent on the preparation method final, sintered products with different morphology and bulk density (measured according to DIN ISO 697 (1984-01)) are obtained. The bulk density of e.g. wet-phase prepared amorphous tricalciumphosphate is often higher than 500 kg/m$^3$, whereas the product produced by the method of the present invention is in the range of 100 to 300 kg/m$^3$. The bulk density of alpha-tricalciumphosphate or beta-tricalciumphosphate produced by state of the art high temperature solid state reaction is in the range of 1000 to 2000 kg/m$^3$ whereas respective products produced by the method of the present invention have bulk densities of below 800 kg/m$^3$ for beta-tricalciumphosphate and below 500 kg/m$^3$ for alpha-tricalciumphosphate.

The specific surface area (measured by nitrogen adsorption at −196° C. according to the BET-method) of state of the art alpha-tricalciumphosphate is below 2 m$^2$/g, whereas alpha-tricalciumphosphate produced according to the present invention has more than 3 m$^2$/g, often and preferably more than 5 m$^2$/g and more preferably more than 8 m$^2$/g. The specific surface area of state of the art beta-tricalciumphosphate is below 0.8 m$^2$/g, whereas beta-tricalciumphosphate of the present invention has more than 1 m$^2$/g, often and preferably more than 1.5 m$^2$/g and more preferably more than 2 m$^2$/g.

Preferred metal salts of the present invention are biomaterials.

Such metal salts may be used in medical applications, e.g. as bone cement and/or resorbable material for implants, as additive to tooth pastes, e.g. as fluoride source and/or abrasive aid, as fluoride source in foodstuffs, e.g. chewing gums, sweets and table salt, as catalyst support, as molecular sieve, as filler for polymers, as UV stabilizer and/or degradation activator in biodegradable or bioresorbable materials.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 2A is the picture of tricalcium phosphate as-prepared, i.e. before sintering.

MODES FOR CARRYING OUT THE INVENTION

The invention is now further described for calcium phosphates, in particular calcium phosphates that are suitable as biomaterials.

In the scope of the present invention it has been found that flame synthesis offers a most versatile tool to materials that due to the resulting morphology, the high purity and the obtainable high crystal phase content are applicable as biomaterials. Furthermore, the direct gas-phase process allows facile substitution of both cations and anions.

Reproducible preparation of tricalcium phosphate (Ca/P=1.5) and different apatites (Ca/P=1.67) offers a challenge to conventional methods. By the inventive method materials with an accurately defined calcium to phosphorous molar ratio Ca/P ranging from 1.425 to 1.67 are obtainable. Such materials optionally may be doped with other anions or cations such as magnesium, zinc, barium, gadolinium, silicate, sulfate or fluoride. Tricalcium phosphate samples with an excess of either calcium or phosphorous are designated with their additional atomic fraction in respect of the stoichiometric sample (stoichiometric sample Ca/P=1.5). Tricalcium phosphate with an excess of calcium (Ca/P>1.5) is marked e.g. "+2.5at % Ca", and tricalcium phosphate with an excess phosphorous (Ca/P<1.5) is marked e.g. "+2.5at % p". A comparison of the Ca/P ratio and the respective at % is shown in Table 1.

TABLE 1

| Theoretical Ca/P molar ratio | expressed as additional at % over stoichiometric |
| --- | --- |
| 1.425 | +5at % P |
| 1.4624 | +2.5at % P |
| 1.485 | +1at % P |
| 1.5 Ca$_3$(PO$_4$)$_2$ | stoichiometric |
| 1.515 | +1at % Ca |
| 1.5375 | +2.5at % Ca |
| 1.575 | +5at % Ca |
| 1.67 (hydroxyapatite) | +11.1at % Ca |

The desired composition, i.e. fluorapatite (FAp), hydroxyfluoapatite (OHFAp/HFAp) and/or any doping can be obtained by admixing the respective anions or cations to the initial solution. By e.g. admixing magnesium octoate, zinc naphthenate, trifluoracetic acid or mixtures thereof to the calcium and phosphate precursor solution, magnesium and/or zinc doped materials and/or fluorapatite $Ca_{10}(PO_4)_6F_2$) or hydroxyfluorapatite ($Ca_{10}(PO_4)_6(OH)F$)can be manufactured in a single step. Beyond doped calcium phosphate, also pure metal salts of other metals than calcium can be obtained by the same method. Similarly, metal salts with an anion other can phosphate can be made. Examples of other materials are calcium carbonate (limestone) nanoparticles or anhydrite nanoparticles ($CaSO_4$) which are described in the experimental section.

Figure 2B:
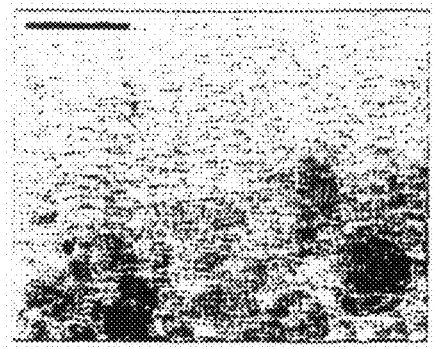
FIG. 2B shows the reduction in specific surface area due to thermal treatment of as-prepared material as shown in FIG. 2A.
Figure 2B:
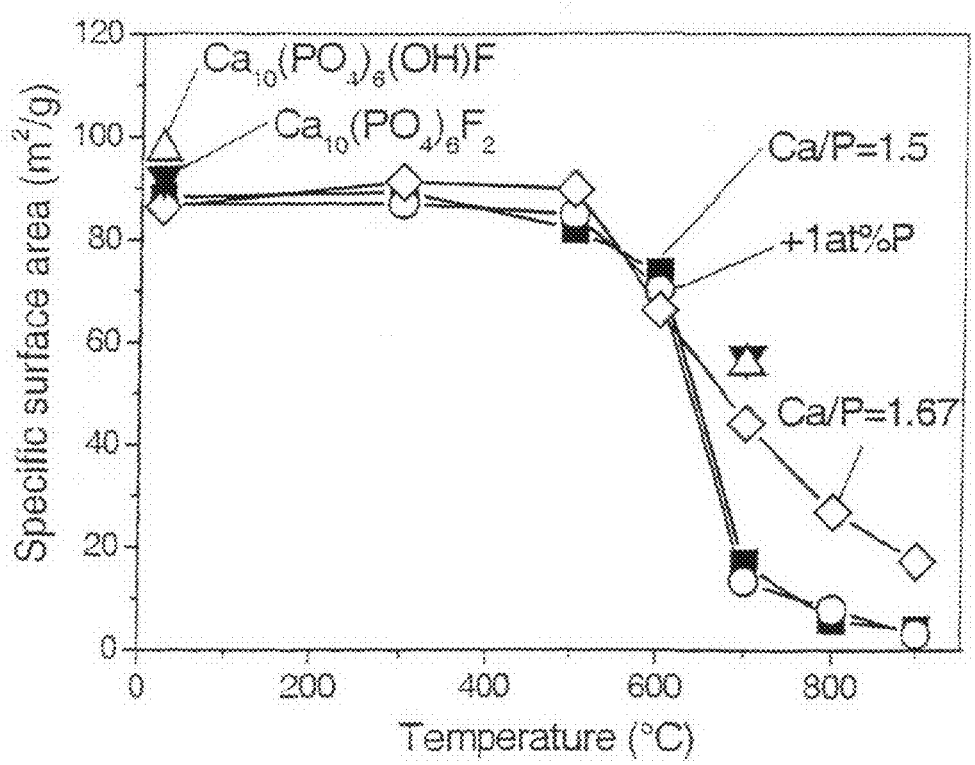

Spherical, highly agglomerated particles of 10-30 nm diameters (FIG. 2A) can be collected after synthesis. Thermal stability and evolution of different crystal phases can be monitored by nitrogen adsorption (BET) and X-ray diffraction (XRD). Samples typically start with 90 $m^2g^{-1}$ (BET equivalent diameter 20 nm) and calcination results in a steep decrease of specific surface area around 600° C. showing the onset of strong sintering and crystallization. While a slight excess of phosphorous (+1 at % P) has no significant influence on the thermal stability of tricalcium phosphate (Ca/P=1.5), hydroxyapatite (Ca/P=1.67) is considerably more stable and maintains above 15 $m^2g^{-1}$ at 900° C. Half ($Ca_{10}(PO_4)_6(OH)F$) and fully ($Ca_{10}(PO_4)_6F_2$) substituted fluorapatite were more resistant to sintering than unsubstituted hydroxyapatite.

Figure 3:
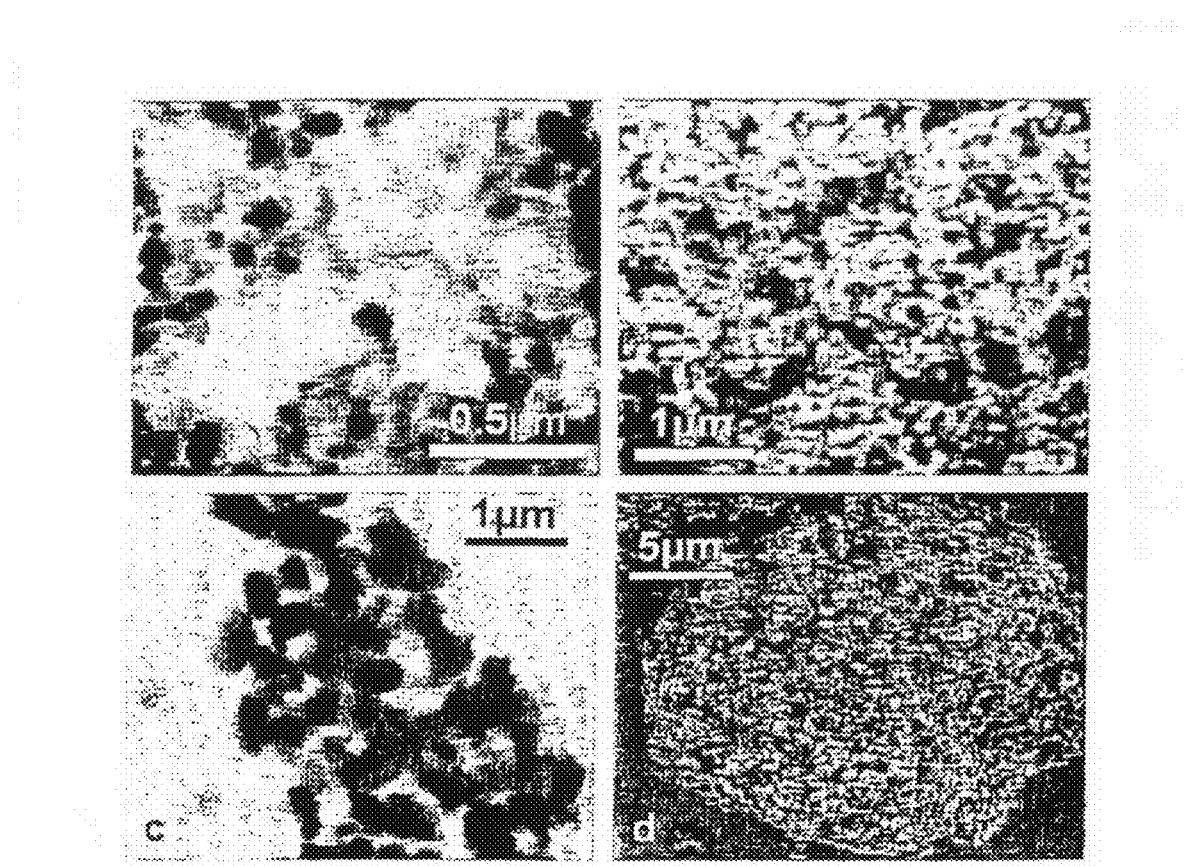
FIG. 3 shows transmission electron microscopy pictures (left two pictures) and scanning electron microscopy images (right two pictures) of calcium phosphate (Ca/P=1.5) after sintering at 700° C. (top two pictures) and after sintering at 900° C. (bottom two pictures).

In vivo histological behavior of biomaterials can be determined by morphology and phase composition. Macropores (diameter >100 μm) have been found to provide a scaffold for bone cell colonization[16] and therefore favour bone ingrowth[17,18]. The content of micropores (diameter <10 μm) is given by the preparation method and the temperature and duration of sintering. Interconnective microporosity guarantees body fluid circulation and is even believed to be responsible for the observed osteoinductive properties of certain bioceramics[19-24]. Electron microscopy images of Ca/P=1.5 prepared by the inventive method after calcination at 700° C. (FIG. 3, pictures a and b) revealed that the material had fused together building clearly visible sinter necks. This sintered product preserves a high porosity with a primary particle size of about 100 nm. Sintering at 900° C. (FIG. 3, pictures c and d) results in much larger primary particles of approximately 0.5 μm in diameter. The highly regular structure with interconnecting micropores provides both sintered products with excellent resorption properties and furthers the induction of bone formation in vivo. Such structures are also described as percolating phases.

Figure 4:
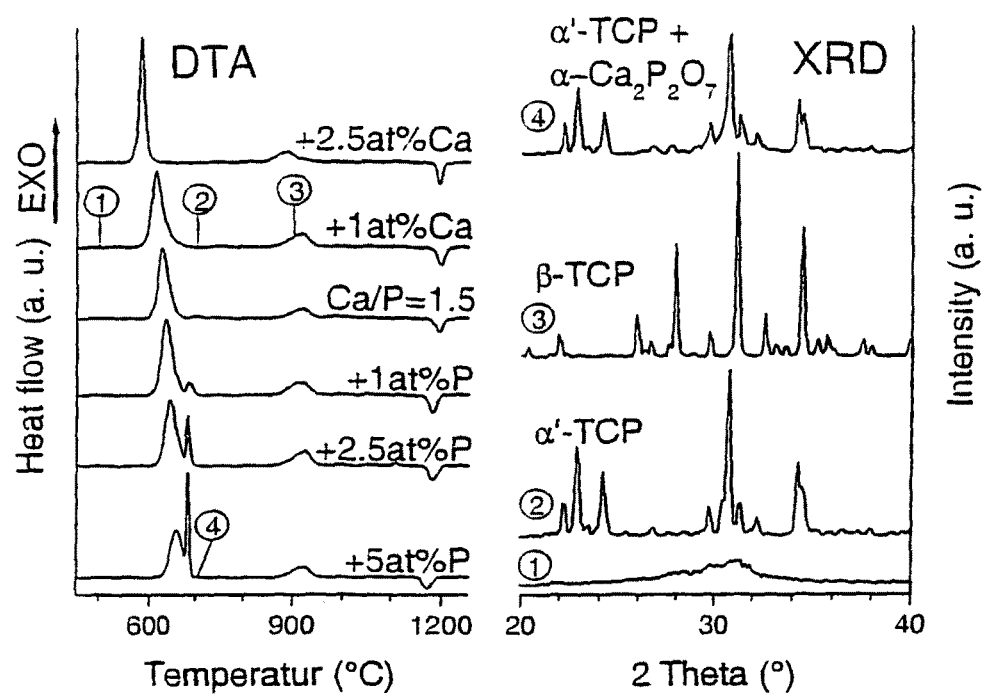
FIG. 4 shows the differential thermo analysis (DTA) data of Ca/P=1.5 samples with different excesses In P and Ca in a temperature range from RT to 1320° C. and at a heating rate of 10° C./min (left side) and the X-ray diffraction pattern of some Ca/P samples after thermal treatment at specific temperatures (right side).
Figure 5:
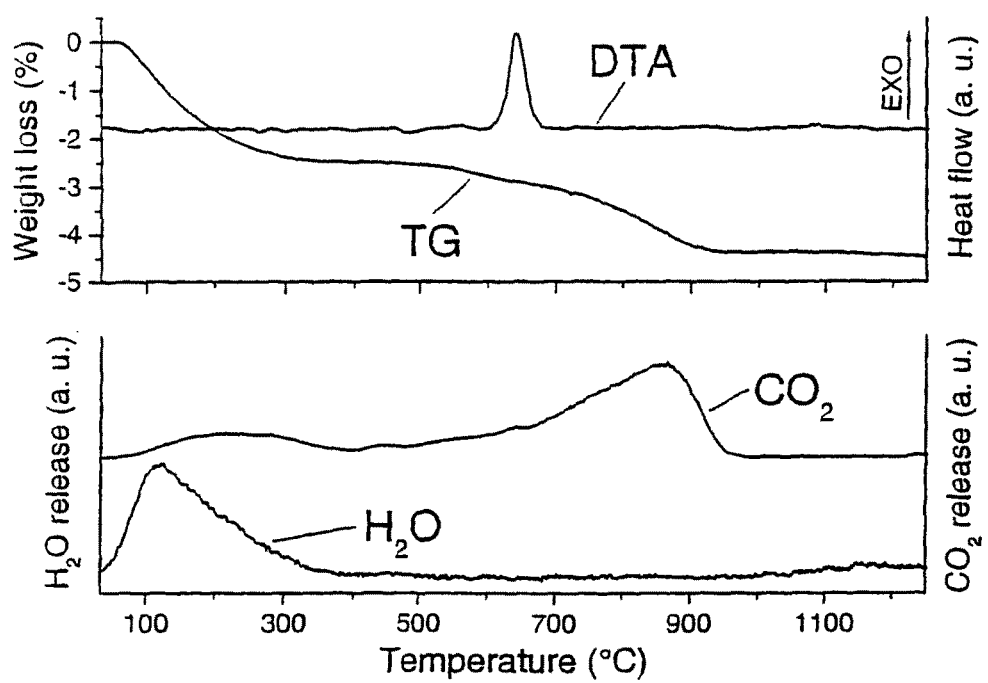
FIG. 5 shows the theromographimetric analysis (TG, top graph) of a Ca/P=1.67 sample and the corresponding differential scanning calorimetric trace (DTA, top graph) with a single exothermic peak showing the crystallization of the sample. The bottom graph depicts carbon dioxide ($CO_2$) and water ($H_2O$) evolution as measured simultaneously by a mass spectrometer that was coupled to the TG/DTA analysis. This setup allows simultaneous detection of crystallization, gas release and mass loss.
Figure 6:
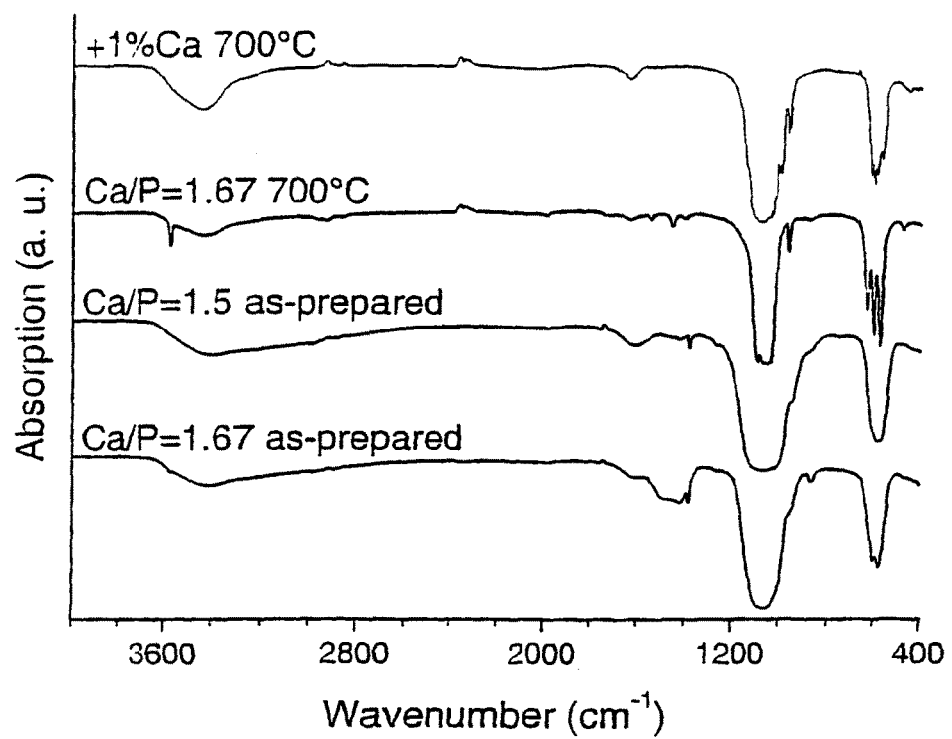
FIG. 6 shows Fourier transform infrared (FTIR) spectra of samples with different Ca/P ratio as-prepared and after treatment at 700° C.
Figure 8:
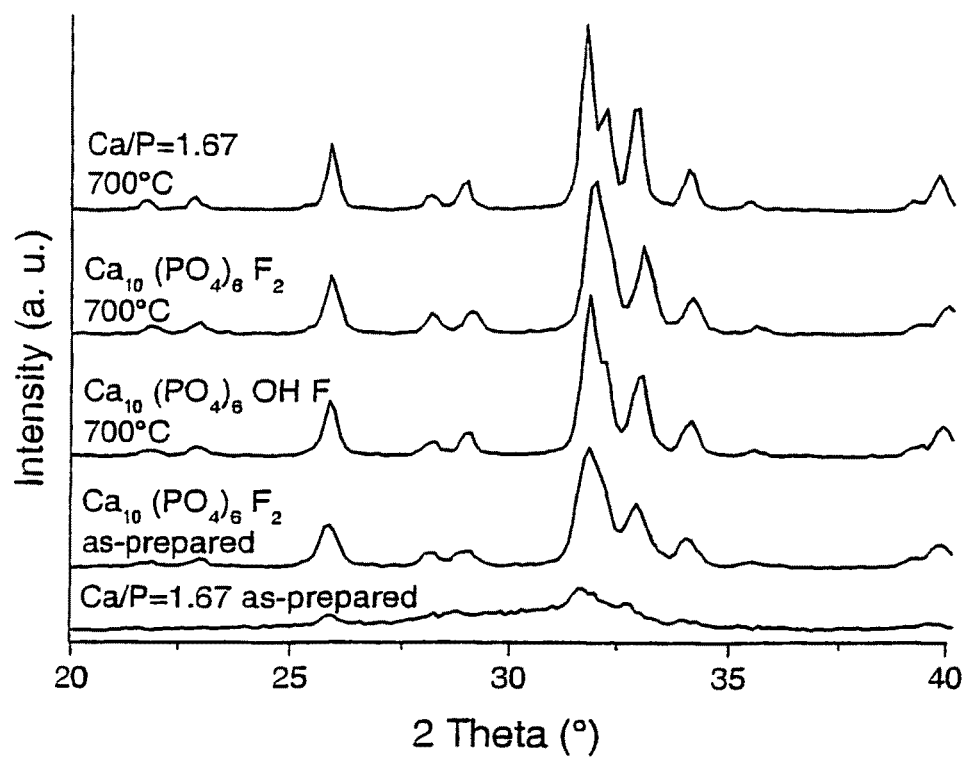
FIG. 8 compares the XRD pattern of several apatites as-prepared and after temperature treatment at 700° C.

As-prepared calcium phosphate consists of amorphous nanoparticles indicating that the fast cooling after the formation in the flame did not allow the material to crystallize. In the scope of the present invention, it has now also been found that such amorphous calcium phosphate can be heat treated at different temperatures to crystallize in a selected crystallinic phase in high selectivity/purity. The presence of a glassy structure of the product as-prepared has been confirmed by differential thermal analysis. A coupled mass spectroscopy (DTA-MS) apparatus allowed simultaneous detection of desorbing water and carbon dioxide. The combination of DTA and XRD patterns (FIG. 4) allows to confirm crystallization and phase transformations. The exothermic peak around 600° C. correlates to the crystallization of the amorphous material. The sample +1% at Ca, amorphous at 500° C. (FIG. 4, label 1), crystallizes to meta-stable $\alpha$-TCP[25], often referred to as $\alpha'$-TCP (FIG. 4, label 2). At 915° C. $\alpha'$-TCP transforms into the thermodynamically favoured $\beta$-TCP (FIG. 4, label 3). At 1190° C., $\beta$-TCP transforms back into the high-temperature polymorph $\alpha$-TCP. Adding excess phosphorous to the $Ca_3(PO_4)_2$ stoichiometry (Ca/P=1.5) provokes the formation of pyrophosphate $Ca_2P_2O_7$. Crystallization of $\alpha$-dicalcium pyrophosphate results in a second peak at 690° C. slightly above the crystallization of tricalcium phosphate (FIG. 4 label 4). The ratio of pyrophosphate to TCP follows the stoichiometry. Minute amounts of pyrophosphate are present in the stoichiometric sample (Ca/P=1.5), they fully vanish with a slight calcium excess (+1at % Ca). For all samples a change in weight due to absorbed water on the high-surface materials was detected by thermo-gravimetry (TG) below 520° C. Unlike calcium phosphates prepared by wet-phase chemistry, the weight loss of flame-made Ca/P ceramics does not exceed 4%. The Ca/P=1.67 sample crystallizes above 600° C. (FIG. 5 top) to hydroxyapatite (XRD pattern, FIG. 8). No further phase transformation or decomposition was detected up to 1250° C. A second weight loss (2%) occurred between 500° C. and 950° C. (FIG. 5 top). This weight loss correlates to the release of CO2 (FIG. 5 bottom) and was already previously attributed to the decomposition of carbonate in apatite[26,27]. The presence of carbonate results in absorption peaks between 1490 $cm^{-1}$ and 1420 $cm^{-1}$ and around 870 $cm^{-1}$ in the Fourier transform infrared (FTIR) spectra[28,29] (FIG. 6). The as-prepared Ca/P=1.5 sample does not show any of these carbonate absorptions. Broad unresolved absorption bands of phosphate around 1060 $cm^{-1}$ and 580 $cm^{-1}$ verify the amorphous structure of the materials after preparation (FIG. 6). Clear absorption peaks are obtained after crystallization and correspond to hydroxyapatite[30] for Ca/P=1.67 and to $\alpha'$-TCP[31] for +1 at % Ca. Weak water absorption bands are found around 3400 $cm^{-1}$ and 1660 $cm^{-1}$ with varying intensity. The crystallized hydroxyapatite still shows minor absorption bands between 1550 $cm^{-1}$ and 1400 $cm^{-1}$ due to residual carbonate[28,29]. From the TG curves the carbonate content can be calculated and was found to be 6.6 wt % $CaCO_3$ which is similar to the carbonate content (3-8 wt %) in human bone[32,33]. Carbonate increases the solubility of hydroxyapatite and results in enhanced biodegradation[9,34,35].

Figure 7:
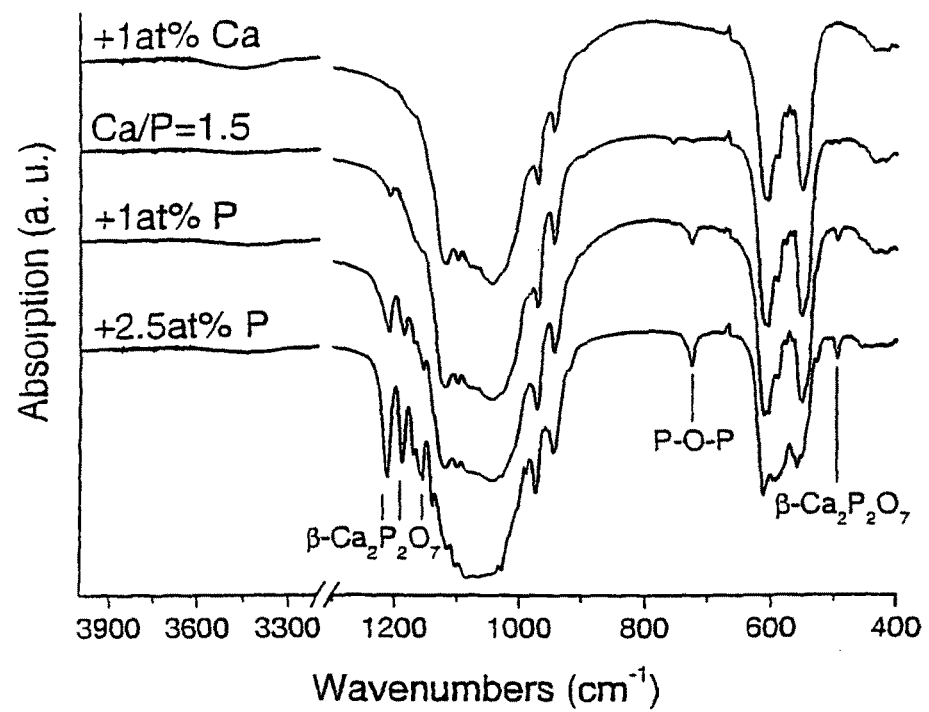
FIG. 7 shows FTIR spectra of samples with different Ca/P ratio after calcination at 900° C. for 30 minutes.

The evidence of calcium pyrophosphate in biomaterials is routinely done by FTIR spectroscopy. Spectra of the samples calcined at 900° C. (FIG. 7) indicating the presence of $Ca_2P_2O_7$ from DTA/XRD measurements show very sharp peaks underlining the high crystallinity of the material. The peak group in the range of 1215 $cm^{-1}$ to 1140 $cm^{-1}$ and two clear peaks at 727 $cm^{-1}$ and 496 $cm^{-1}$, to be best seen in the sample +2.5at % P, correspond to $\beta$-calcium pyrophosphate ($\beta$-$Ca_2P_2O_7$) absorption bands and are consistent with literature[36-38]. A continuous decrease of absorption for these bands is seen by decreasing the phosphorous content. In agreement with DTA measurements the pyrophosphate present in the sample is determined by an excess of phosphorous in the precursor. Consequently, the suppression or promotion of the formation of calcium pyrophosphate can be accessed by varying the Ca/P ratio in the precursor. No Calcium pyrophosphate was detected in the sample +1 at % Ca by DTA and FTIR, where the infrared spectrum matches well with the one of $\beta$-TCP[31,39].

Figure 10:
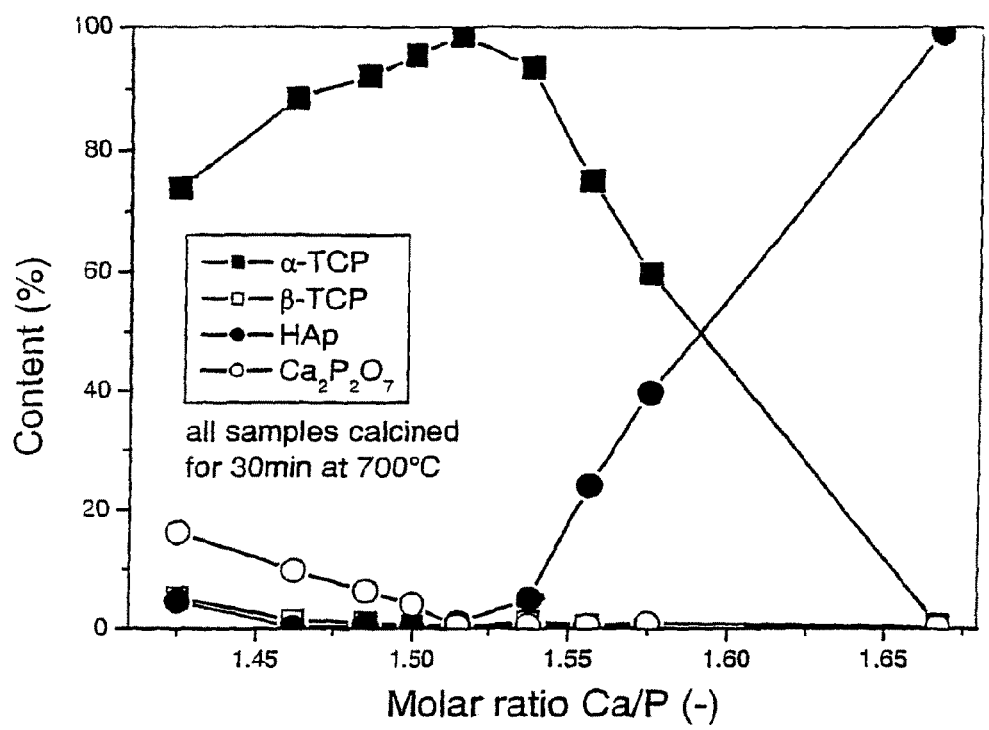
FIG. 10 shows the formation of different calcium phosphates dependent on the Ca/P ratio after calcinations at 700° C. for 30 minutes.
Figure 11:
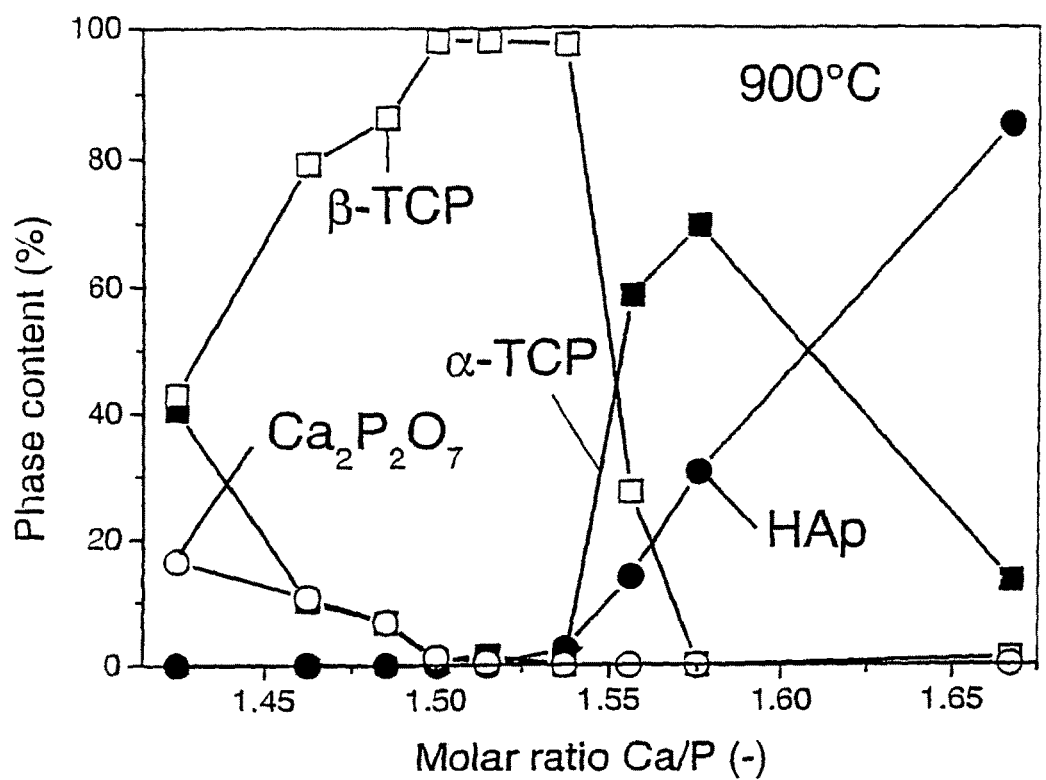
FIG. 11 shows the formation of different calcium phosphates dependent on the Ca/P ratio after calcinations at 900° C. for 30 minutes.

The formation of a specific product is dependent on the Ca/P ratio as well as of the calcinations temperature (see FIGS. 10 and 11). Almost pure alphatricalcium phosphate is obtained at a Ca/P ratio slightly above 1.5 but below 1.55 and 30 minutes calcination at 700° C. (FIG. 10). Almost pure hydroxyapatite is obtained at a Ca/P ratio of about 1.67 and 30 minutes calcinations at 700° C. (FIG. 10). For the production of almost pure beta-tricalcium phosphate the same Ca/P ratio can be chosen as for the production of alpha-tricalcium phosphate, but the calcination temperature has to be enhanced to 900° C. (FIG. 11).

TABLE 2

| Sample name | Theoretical Ca/P ratio | Measured Ca/P ratio | error |
|---|---|---|---|
| Ca/P = 1.5 | 1.500 | 1.50 | 0.01 |
| +1at % Ca | 1.515 | 1.51 | 0.01 |
| Ca/P = 1.67 | 1.667 | 1.64 | 0.01 |
| Commercial ref. (see below) | 1.500 | — | — |

Commercial reference examples are e.g.:
CalciResorb (manufactured by Céraver Ostéal), characterized by FTIR and XRD: TCP content >96 wt %, less than 4 wt % Hydroxyapatite. Composition: 1.48<Ca/P<1.51.
Biosorb (SBM S.A.)r more than 95 wt % TCP, Composition: 1.49<Ca/P<1.51.
Bioresorb (Oraltronics), phase pure (>95 wt % TCP).

Figure 9:
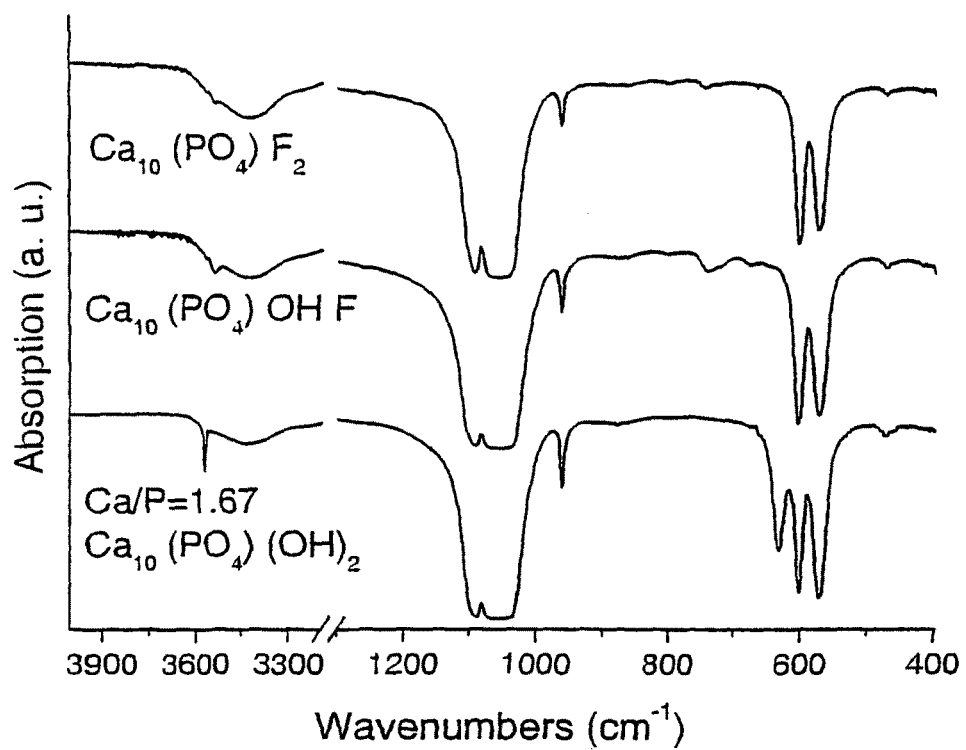
FIG. 9 compares the FTIR spectra of hydroxyapatite, hydroxyfluorapatite and fluorapatite after calcination at 700° C.

The application of calcium phosphate biomaterials is not restricted to hydroxyapatite and tricalcium phosphate. Recent studies about alternative calcium phosphate materials have focused on fluoride substituted hydroxyapatite. As shown above r fluoride substituted apatites can easily be obtained by the method of the present invention. Differentiation of fluorapatite and hydroxyfluorapatite from hydroxyapatite can be done by FTIR spectroscopy. Spectra of the three apatites after calcination at 700° C. are shown in FIG. 9. Fluoride comprising apatites, due to them being neutral with regard to calcium content in the animal body can not only be used as substitutes for fluorapatite but also as a non-toxic fluoride source.

Figure 12:
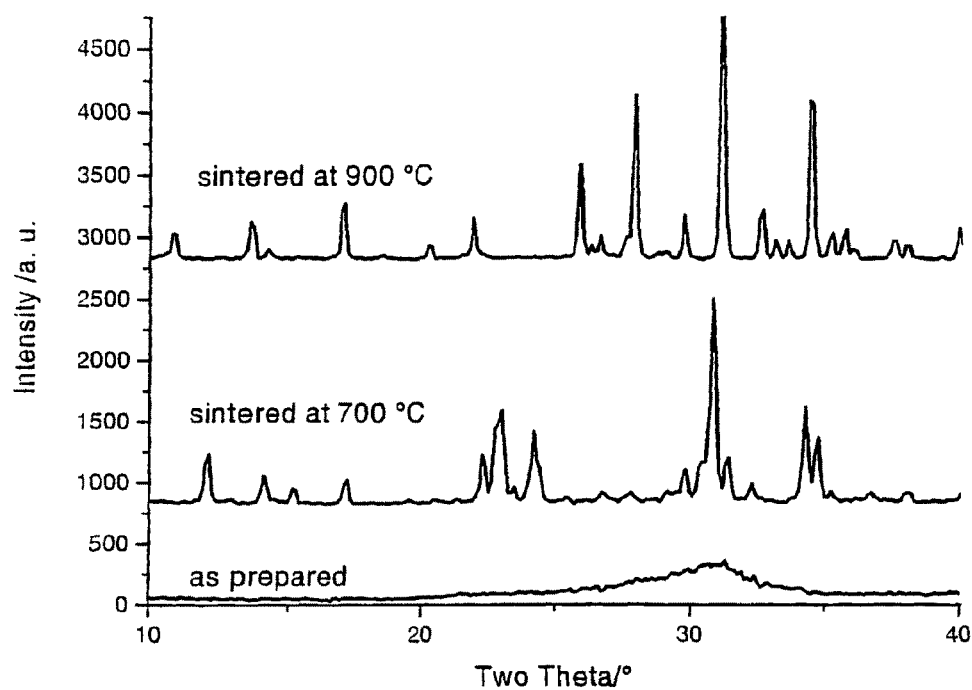
FIG. 12 shows that in magnesium doped tricalcium phosphate containing 1 atom-% Mg with respect to calcium no separate phase is visible and the XRD pattern corresponds to alpha-TCP (after 700° C. sintering) or beta-TCP (after 900° C. sintering). This corroborates the good dispersion and incorporation of Mg in the lattice.
Figure 13:
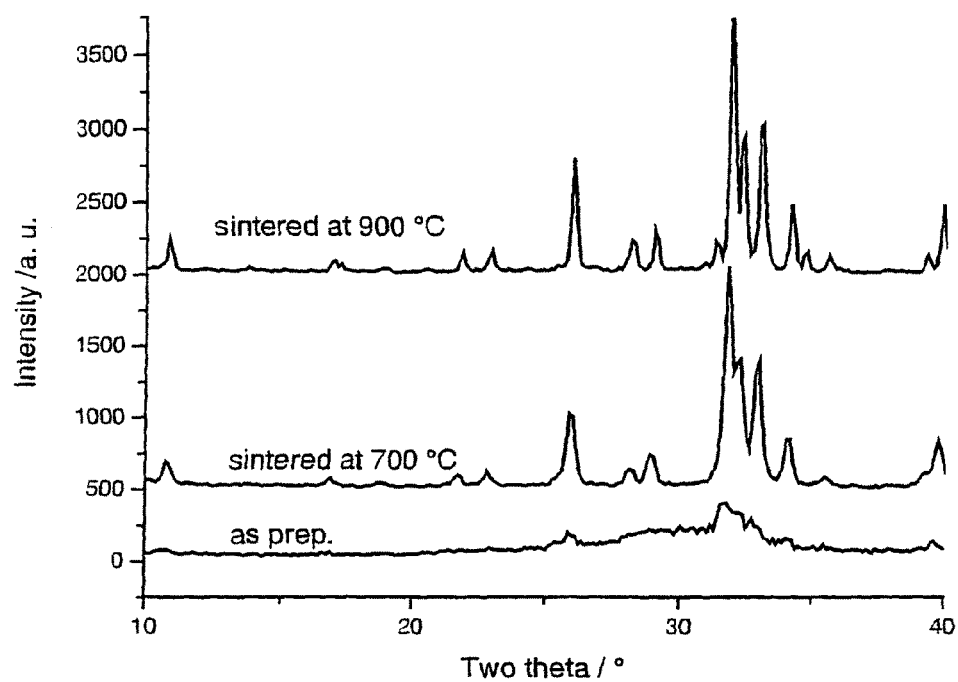
FIG. 13 shows that in magnesium doped apatite containing 1 atom-% Mg with respect to calcium no separate phase is visible and the XRD pattern corresponds to hydroxyl apatite (after 700° C. sintering) and remains stable (after 900° C. sintering). This corroborates the good dispersion and incorporation of Mg in the lattice.
Figure 14:
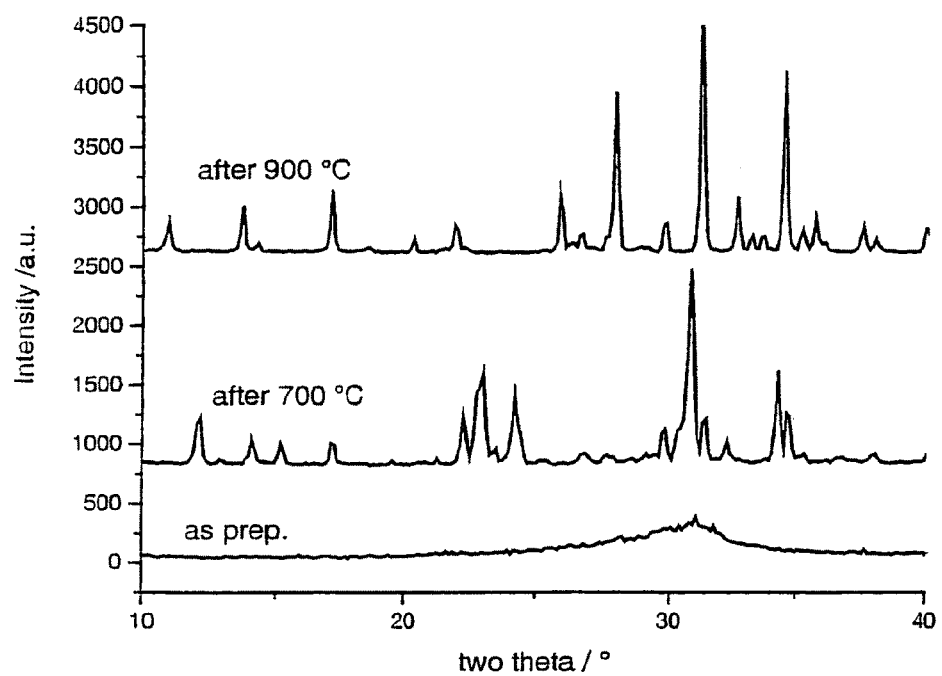
FIG. 14 shows that in zinc doped tricalcium phosphate containing 1 atom-% Zn with respect to calcium no separate phase is visible and the XRD pattern corresponds to alpha-TCP (after 700° C. sintering) or beta-TCP (after 900° C. sintering). This corroborates the good dispersion and incorporation of Zn in the lattice.
Figure 15:
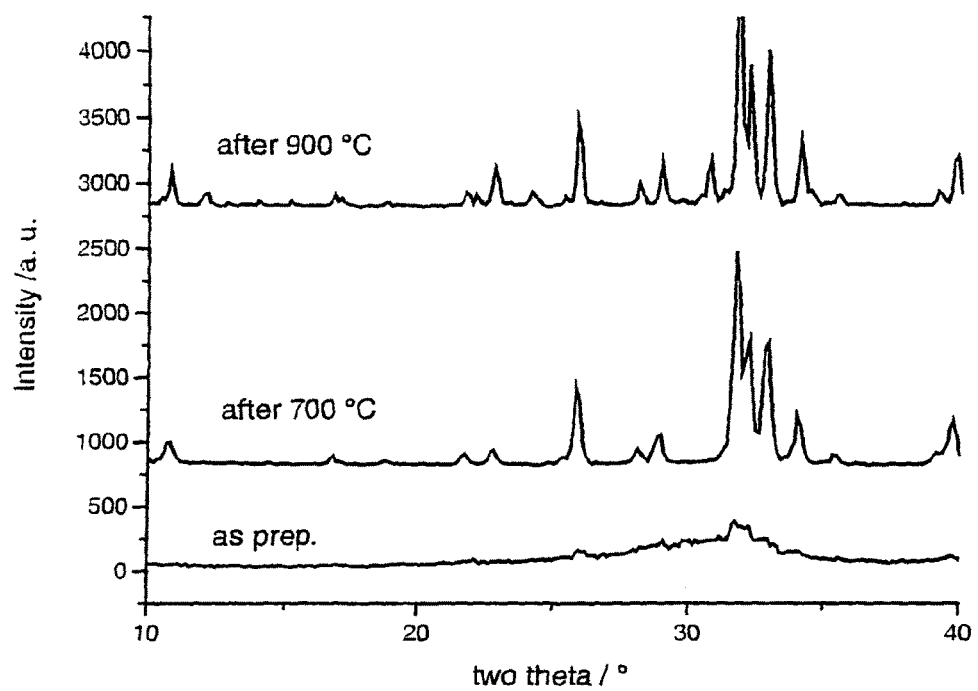
FIG. 15 shows that in zinc doped apatite containing 1 atom-% Zn with respect to calcium no separate phase is visible and the XRD pattern corresponds to hydroxyl apatite (after 700° C. sintering) and remains stable (after 900° C. sintering). This corroborates the good dispersion and incorporation of Zn in the lattice.

By adding a magnesium source such as magnesium octoate in desired amounts (e.g. 1 at-%) to the precursor mixture for the preparation of tricalciumphosphate the corresponding doped calcium phosphate polymorph phases can be prepared without phase segregation such as the segregation of MgO rich phases. Thus, by the method of the present invention phase pure magnesium doped metal salts, such as amorphous tricalciumpholphate, alpha-tricalciumpholphate, beta-tricalciumpholphate, or apatites, can be produced (see FIG. 12 and FIG. 13). Similar results are obtained using a zinc source such as zinc naphthenates or zinc octoates (see FIG. 14 and FIG. 15).

Figure 16:
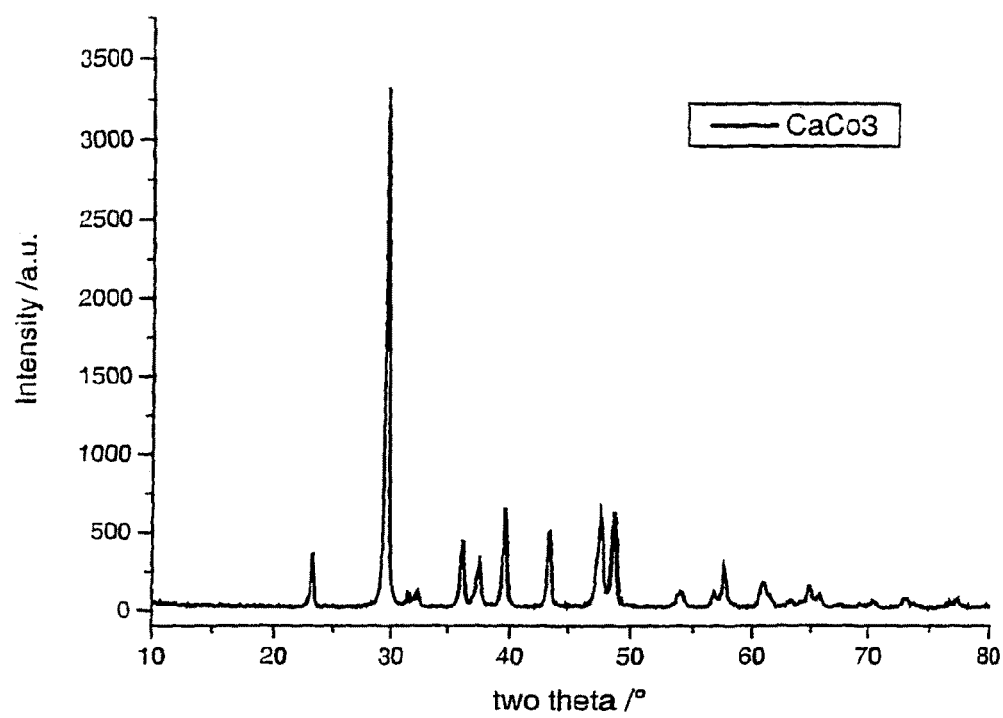
FIG. 16 shows that the XRD pattern for calcium carbonate nanoparticles prepared by flame spray synthesis corresponds to calcium carbonate with some impurity of calcium oxide. These particles of the invention are made in a single step from calcium octoate in a flame spray burner.
Figure 17:
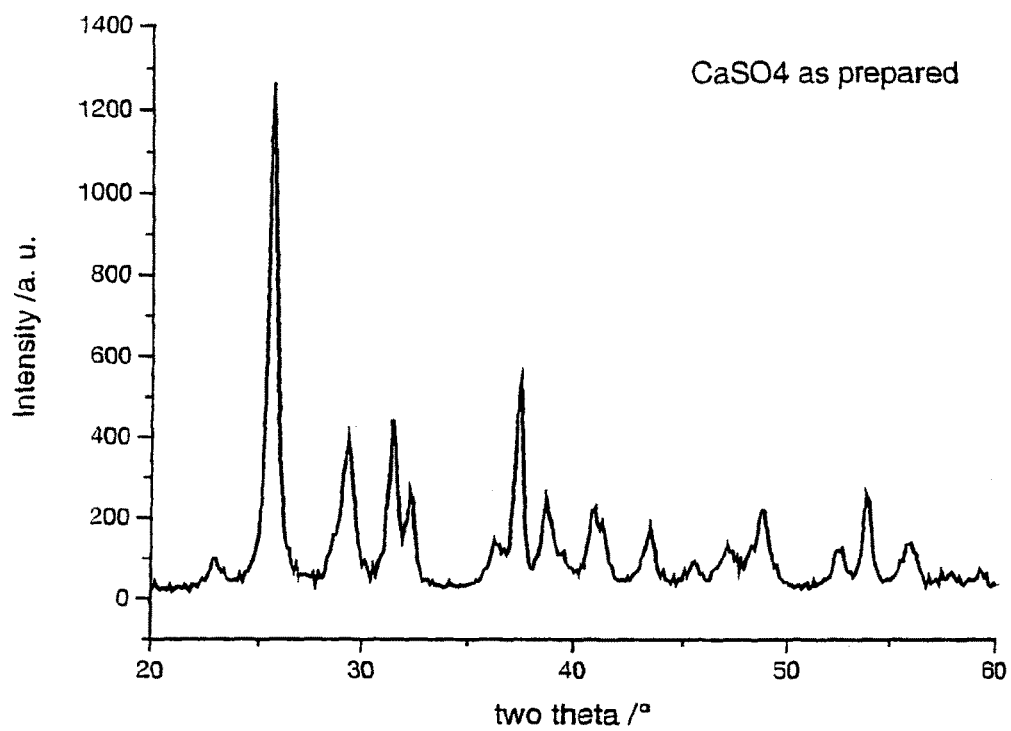
FIG. 17 shows the XRD of anhydrite (calcium sulfate) nanoparticles, obtained by feeding calcium octoate and dimethylsulfoxide (DMSO) into a flame spray burner. Small amounts of calcium oxide are present.

Other metal salts can be obtained as described above for calcium and phosphate comprising salts. By e.g. using a calcium source such as calcium octoate and a carbonate source such as a hydrocarbon or the calcium octoate itself, calciumcarbonate is obtained (see FIG. 16) and by using the above described calcium source together with a sulfate source, e.g. dimethylsulfoxide (DMSO), calcium sulfate is obtained (see FIG. 17).

EXAMPLES

Powder Preparation

Figure 1A:
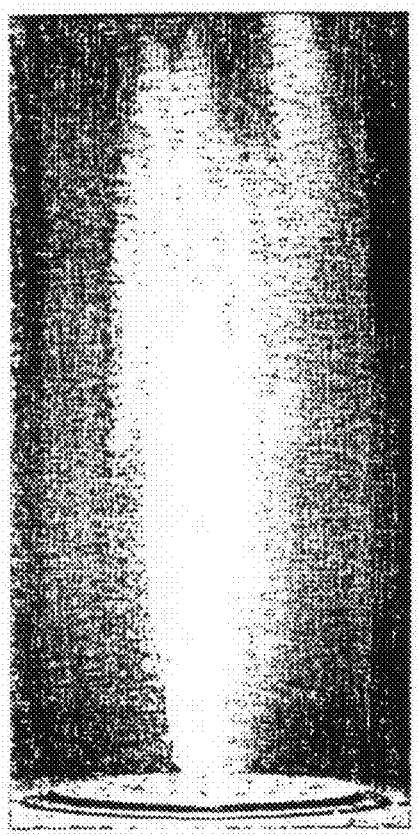
FIG. 1A shows the flame of a 2-phase nozzle burner where a spray of metal containing liquid is dispersed and ignited. The burning spray is the reactor itself. Particles form from this hot gas and can be collected on top of the burner.
Figure 1B:
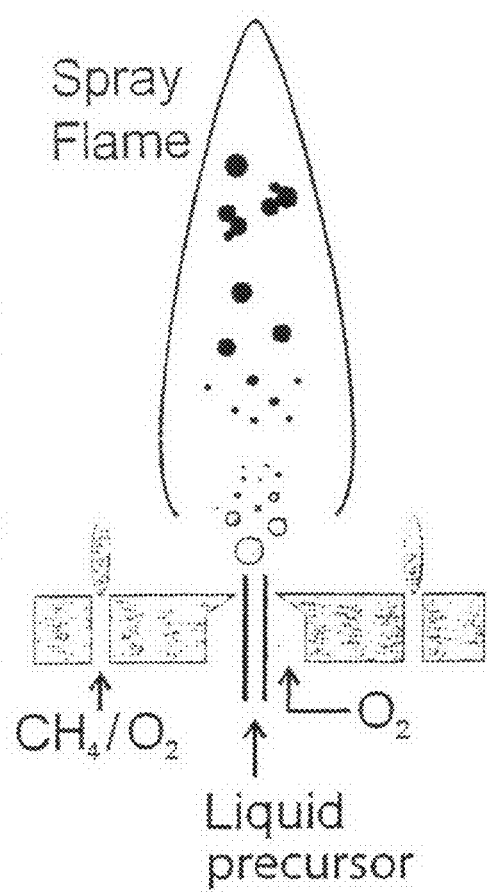
FIG. 1B is a schematic presentation of the flame indicating the material streams.

Calcium phosphate biomaterials were prepared by flame spray pyrolysis using calcium oxide (99.9%, Aldrich) dissolved in 2-ethylhexanoic acid (purum., ≥98%, Fluka) and tributyl phosphate (puriss., ≥99%, Fluka) as precursors. The calcium content of the Ca precursor was determined by complexometry with ethylenediaminetetraacetic acid disodium salt dihydrate (ref.) (≥99%, Fluka) to be 0.768 mol kg$^{-1}$. Starting from a parent solution (38 ml per run) with a calcium to phosphorous molar ratio (Ca/P) of 1.5, the various mixtures ranging from 1.425≤Ca/P≤1.667 have been obtained by adding corresponding amounts of either calcium 2-ethylhexanoate or tributyl phosphate. For the half ($Ca_{10}(PO_4)_6OH\ F$) and fully ($Ca_{10}(PO_4)_6F_2$) fluorine substituted hydroxyapatites, tri-fluoroacetic acid (>99%, Riedel deHaen) has been correspondingly mixed with precursors having a molar ratio of Ca/P=1.67. Throughout all the experiments the concentration of the precursor solutions was kept constant (0.667 mol L$^{-1}$) by adding xylene (96%, Riedel deHaen). The liquid mixtures were fed through a capillary (diameter 0.4 mm) into a methane/oxygen flame at a rate of 5 ml min$^{-1}$. Oxygen (5 L min$^{-1}$, 99.8%, Pan Gas) was used to disperse the liquid leaving the capillary. The pressure drop at the capillary tip (1.5 bar) was kept constant by adjusting the orifice gap area at the nozzle. A stable combustion was achieved by applying a sheath gas (oxygen, 230 L h$^{-1}$, 99.8%, Pan Gas) through a concentric sinter metal ring (see FIG. 1A, 1B). Calibrated mass flow controllers (Bronkhorst) were used to monitor all gas flows. The as formed particles were collected on a glass fibre filter (Whatmann GF/A, 15 cm in diameter) which was placed on a cylinder mounted above the flame by the aid of a vacuum pump (Vaccubrand). Thermal treatment (30 min at specified temperature) was conducted in a preheated laboratory furnace (Thermolyne Type 48000) followed by quenching in air at ambient conditions.

Powder Characterization

The specific surface area of the powders was analyzed on a Tristar (Micromeritics Instruments) by nitrogen adsorption at 77 K using Brunauer-Emmett-Teller (BET) method. All samples were outgassed at 150° C. for 1 hour. The X-ray diffraction spectroscopy (XRD) data were collected on a Burker D 8 Advance diffractometer from 20° to 40° at a step size of 0.12° and a scan speed of 2.4° min$^{-1}$ at ambient condition. For Fourier transform infrared (FTIR) spectroscopy, pellets of 200 mg KBr (≥99.5%, Fluka) and 0.5-0.7 mg sample were prepared and dehydrated in a drying furnace (VT 6025, Gerber Instruments) at 80° C./<10 mbar for at least 8h before examination (400 cm$^{-1}$<λ<4000 cm$^{-1}$) on a Perkin Elmer Spectrum BX (4 scans) with 4 cm$^{-1}$ resolution. Elemental analysis was performed by laser ablation ion-coupled plasma mass spectroscopy (LA-ICP-MS). Samples were pressed into plates and irradiated with an excimer laser (Lambda Phisyk Compex 110 I; ArF, 193 nm, pulse energy 150 mJ, frequency 10 Hz). The vaporized material was carried by a helium stream to an ICP mass spectrometer (Perkin Elmer Elan 6100) and analyzed for calcium and phosphorous. As an internal standard a fluorapatite (Durango) was used. The transmission electron microscopy (TEM) pictures were recorded on a CM30 ST (Philips, LaB6 cathode, operated at 300 kV, point resolution ~2 Å). Particles were deposited onto a carbon foil supported on a copper grid. Scanning electron microscopy (SEM) investigations were performed with a Leo 1530 Gemini (Zeiss).

Detailed Preparation Example 111 g calcium oxide (Aldrich, >99%) are dissolved in 1980 g 2-Ethylhexanoic acid (Fluka, 99%) and 20 ml of acetic anhydride (Fluka, >99%) by heating the mixture to 140° C. under reflux. After cooling some remaining calcium acetate is removed by decanting the clear solution. After adding toluene, a 0.768 M solution is obtained as determined by titration using Ethylendiamine-tetraacetate-disodium salt (Fluka, 99%) and Eriochromschwarz-T as an indicator (Fluka, >95%).

0.685 kg of the above solution (stable at room temperature for at least 3 month) are mixed with 93.44 g Tributyl-phosphate (Fluka, puriss, >99%) and toluene added to a total volume of 1 liter at room temperature (298 K). For a single run, 38 ml of this solution are mixed with 2 ml toluene and flame sprayed. Combustion enthalpy of such a precursor liquid is above 25 kJ/g and the viscosity below 10 mPas.

All materials described herein have been prepared at a liquid flow rate of 5 ml/min using a dispersion gas (oxygen, Pan Gas, >99.8%) flow of 5 liters/min.

While all products obtainable by the method of the present invention have a lot of applications, e.g. as catalyst support, as molecular sieve, as filler for polymers and/or as UV stabilizers, due to their natural occurrence in human and non human animals, in particular mammals, the calcium phosphates described above, are much preferred for some applications, e.g.

in dental and medical applications, alone or together with other substances such as preferably biopolymers, such applications comprising the application as bone cement and/or resorbable material for implants, as implant coatings, in the repair of bony defects or peridontal defects, as bone space filler etc., as additive to tooth pastes, e.g. as fluoride source and/or abrasive aid, as fluoride source in foodstuffs, e.g. chewing gums, sweets and table salt, as degradation activator in biodegradable or bioresorbable materials.

In medical applications such as implants and bone cement, the product produced according to the present invention is favorable since it can easily be obtained in high purity, and since it can be sintered to form a product with desired percolating phases (interconnected pores), probably due to the extremely light and open structure of the aerogel that is used as a starting material. Combined with low amounts of water, few sintering and a reduced volume loss compared to conventionally prepared powder assure a maximum degree of interconnected porosity. Another great advantage of the materials produced by the method of the present invention is that they can be doped with e.g. barium and/or gadolinium such that the degradation of a bioresorbable material can be controlled by non-invasive methods such as X-ray imaging or nuclear magnetic resonance imaging.

As ingredient to tooth pastes in particular fluorapatite is preferred. It is known that hydroxidefluoride-exchange in apatite is very fast such that fluorapatite can replace the hitherto used fluoride source in tooth pastes. Since, however, fluorapatite is "calcium neutral", i.e. does not affect the calcium content of the body, in particular the teeth and the bones, the amount of it is uncritical such that it can be added in much higher amounts than other fluoride sources and simultaneously act as e.g. abrasion aid to improve the plaque removal.

The above addressed benefit of fluorapatite also applies with regard to foodstuffs. With hitherto available fluoride sources only very specific foodstuffs such as table salt and water, the maximal intake of which by a person can be estimated, could be fluoride enriched. By using fluorapatite, in view of its being non toxic even in large amounts and its fluoride release properties exclusively making up for a fluoride deficiency in body apatite, a lot of foodstuffs can be supplemented such as e.g. chewing gums, candies, sweets but also the already hitherto fluoride enriched table salt and drinking water. The supplementation of such foodstuffs as chewing gums, candies, sweets (including snacks, cakes, chocolate etc.) and salted snacks, yogurts, and other foodstuffs that are largely consumed during the day when tooth cleaning may be impossible, is much desirable in view of tooth health.

Microorganisms necessary for biodegradation of e.g. biodegradable polymeric materials often need a large amount of specific ions such as calcium and phosphate. Due to the inventive production method not only large amounts of nanoparticulate calcium and phosphates comprising compounds can be obtained, but also doped materials that can be adapted with regard to solubility (e.g. by some $CO_2$ in an apatite) and content of further desirable metals other than calcium.

The products of the present invention in general do not segregate and they improve the flowability/pourability. Thus, they have similar fields of applications as the product AEROSIL® of Degussa.

The products of the present invention can e.g. be used to improve the pourability of e.g. table salt, but also to improve the flowability of tooth pastes or of a solid component in a manufacturing process e.g. an additive in the polymer manufacturing or a spice mixture in the snack production etc. Other applications are as rheology or thixotropy improving agents, as mechanical stability, UV resistance or other features improving additives, as admixtures or fillers not only in biodegradable but also in common plastics.

If suitably doped (for example by adding silver ions into the material), the products of the present invention can also be provided with antibacterial features making them suitable for antibacterially equipped polymers or polymers comprising products such as coatings paints adhesives etc.

While there are shown and described presently preferred embodiments of the invention, it is to be distinctly understood that the invention is not limited thereto but may be otherwise variously embodied and practiced within the scope of the following claims.

REFERENCES

1. Jarcho, M. Calcium-Phosphate Ceramics as Hard Tissue Prosthetics. *Clinical Orthopaedics and Related Research,* 259-278 (1981).
2. de Groot, K. *Bioceramics of Calcium Phosphate* (ed. de Groot, K.) (CRC Press, Boca Raton, 1983).
3. LeGeros, R. Z. *Calcium Phosphates in Oral Biology and Medicine* (ed. LeGeros, R. Z.) (S. Karger, Basel, 1991).
4. Metsger, D. S., Driskell, T. D. & Paulsrud, J. R. Tricalcium Phosphate Ceramic—a Resorbable Bone Implant—Review and Current Status. *Journal of the American Dental Association* 105, 1035-1038 (1982).
5. LeGeros, R. Z., LeGeros, J. P., Daculsi, G. & Kijkowska, R. *Encyclopedic Handbook of Biomaterials and Bioengineering* (eds. Wise, D. L., J., T. D. & E., A. D.) (Marcel Dekker, New York, 1995).
6. Dong, Z. L., Khor, K. A., Quek, C. H., White, T. J. & Cheang, P. TEM and STEM analysis on heat-treated and in vitro plasma-sprayed hydroxyapatite/Ti-6Al-4V composite coatings. *Biomaterials* 24, 97-105 (2003).
7. Cleries, L., Fernandez-Pradas, J. M., Sardin, G. & Morenza, J. L. Dissolution behaviour of calcium phosphate coatings obtained by laser ablation. *Biomaterials* 19, 1483-1487 (1998).
8. Arias, J. L. et al. Micro- and nano-testing of calcium phosphate coatings produced by pulsed laser deposition. *Biomaterials* 24, 3403-3408 (2003).
9. Tadic, D., Peters, F. & Epple, M. Continuous synthesis of amorphous carbonated apatites. *Biomaterials* 23, 2553-2559 (2002).
10. Sarkar, M. R., Wachter, N., Patka, P. & Kinzl, L. First histological observations on the incorporation of a novel calcium phosphate bone substitute material in human cancellous bone. *Journal of Biomedical Materials Research* 58, 329-334 (2001).
11. Overgaard, S., Bromose, U., Lind, M., Bunger, C. & Soballe, K. The influence of crystallinity of the hydroxyapatite coating on the fixation of implants Mechanical and histomorphometric results. *Journal of Bone and Joint Surgery-British Volume* 81B, 725-731 (1999).
12. Knaack, D. et al. Resorbable calcium phosphate bone substitute. *Journal of Biomedical Materials Research* 43, 399-409 (1998).
13. Madler, L., Kammler, H. K., Mueller, R. & Pratsinis, S. E. Controlled synthesis of nanostructured particles by flame spray pyrolysis. *Journal of Aerosol Science* 33, 369-389 (2002).
14. Stark, W. J. et al. Flame-made titania/silica epoxidation catalysts: Toward large-scale production. *Industrial & Engineering Chemist Research* 41, 4921-4927 (2002).
15. Stark, W. J. & Pratsinis, S. E. Aerosol flame reactors for manufacture of nanoparticles. *Powder Technology* 126, 103-108 (2002).
16. Ravaglioli, A. & Krajewski, A. in *Bioceramics: Materials, Properties, Applications* p. 432 (Chapman & Hall, London, 1992).
17. Gauthier, O., Bouler, J. M., Aguado, E., Pilet, P. & Daculsi, G. Macroporous biphasic calcium phosphate ceramics: influence of macropore diameter and macroporosity percentage on bone ingrowth. *Biomaterials* 19, 133-139 (1998).
18. Weiss, P. et al. Synchrotron X-ray microtomography (on a micron scale) provides three-dimensional imaging representation of bone ingrowth in calcium phosphate biomaterials. *Biomaterials* 24, 4591-4601 (2003).
19. Yuan, H. P. et al. Osteoinduction by calcium phosphate biomaterials. *Journal of Materials Science-Materials in Medicine* 9, 723-726 (1998).
20. Bignon, A. et al. Effect of micro- and macroporosity of bone substitutes on their mechanical properties and cellular response. *Journal of Materials Science-Materials in Medicine* 14, 1089-1097 (2003).
21. Yuan, H. P. et al. Bone formation induced by calcium phosphate ceramics in soft tissue of dogs: a comparative study between porous alpha-TCP and beta-TCP. *Journal of Materials Science-Materials in Medicine* 12, 7-13 (2001).
22. Yuan, H. P. et al. A comparison of the osteoinductive potential of two calcium phosphate ceramics implanted intramuscularly in goats. *Journal of Materials Science-Materials in Medicine* 13, 1271-1275 (2002).
23. Yuan, H. P., Li, Y. B., de Bruijn, J. D., de Groot, K. & Zhang, X. D. Tissue responses of calcium phosphate cement: a study in dogs. *Biomaterials* 21, 1283-1290 (2000).
24. Yuan, H. P. et al. A preliminary study on osteoinduction of two kinds of calcium phosphate ceramics. *Biomaterials* 20, 1799-1806 (1999).
25. Somrani, S., Rey, C. & Jamal, M. Thermal evolution of amorphous tricalcium phosphate. *Journal of Materials Chemist* 13, 888-892 (2003).
26. Peters, F., Schwarz, K. & Epple, M. The structure of bone studied with synchrotron X-ray diffraction, X-ray absorption spectroscopy and thermal analysis. *Thermochimica Acta* 361, 131-138 (2000).
27. Suchanek, W. L. et al. Mechanochemical-hydrothermal synthesis of carbonated apatite powders at room temperature. *Biomaterials* 23, 699-710 (2002).
28. Baxter, J. D., Biltz, R. M. & Pellegri. Ed. Physical State of Bone Carbonate—a Comparative Infra-Red Study in Several Mineralized Tissues. *Yale Journal of Biology and Medicine* 38, 456-& (1966).
29. Emerson, W. H. & Fischer, E. E. The Infra-Red Absorption Spectra of Carbonate in Calcified Tissues. *Archives of Oral Biology* 7, 671-683 (1962).
30. Fowler, B. O. Infrared Studies of Apatites. 1. Vibrational Assignments for Calcium, Strontium, and Barium Hydroxyapatites Utilizing Isotopic-Substitution. *Inorganic Chemistry* 13, 194-207 (1974).
31. Jillavenkatesa, A. & Condrate, R. A. The infrared and R~n spectra of beta- and alpha-tricalcium phosphate (Ca-3 (PO4)(2)). *Spectroscopy Letters* 31, 1619-1634 (1998).
32. Dorozhkin, S. v. & Epple, M. Biological and medical significance of calcium phosphates. Angewandte *Chemie-International Edition* 41, 3130-3146 (2002).
33. Daculsi, G., Bouler, J. M. & LeGeros, R. Z. in *International Review of Cytology—a Survey of Cell Biology*, Vol 172 129-191 (ACADEMIC PRESS INC, San Diego, 1997).
34. Fulmer, M. T., Ison, I. C., Hankermayer, C. R., Constantz, B. R. & Ross, J. Measurements of the solubilities and dissolution rates of several hydroxyapatites. *Biomaterials* 23, 751-755 (2002).
35. Nelson, D. G. A. The Influence of Carbonate on the Atomic-Structure and Reactivity of Hydroxyapatite. *Journal of Dental Research* 60, 1621-1629 (1981).
36. Cornilsen, B. C. & Condrate, R. A. Vibrational-Spectra of Beta-Ca2p2o7 and Gamma-Ca2p2o7. *Journal of Inorganic & Nuclear Chemistry* 41, 602-605 (1979).
37. Dewaal, D. & Hutter, C. Vibrational-Spectra of a Solid-Solution of Cadmium and Calcium Pyrophosphate. *Materials Research Bulletin* 29, 1129-1135 (1994).
38. Hezel, A. & Ross, S. D. Vibrational Spectra of Some Divalent Metal Pyrophosphates. *Spectrochimica Acta Part a—Molecular Spectroscopy* A 23, 1583-& (1967).
39. Pena, J. & Vallet-Regi, M. Hydroxyapatite, tricalcium phosphate and biphasic materials prepared by a liquid mix technique. *Journal of the European Ceramic Society* 23, 1687-1696 (2003).
40. Rigby, S. P., R. S. Fletcher, et al. (2004). "Characterisation of porous solids using integrated nitrogen sorption and mercury porosimetry." *Chemical Engineering Science* 59(1): 41-51.
41. W. J. Stark, S. E. Pratsinis, Aerosol flame reactors for manufacture of nanoparticles, *Powder Technol.*, 126, 103-108 (2002).
42. L. Madler, W. J. Stark, S. E. Pratsinis, Flame-made ceria nanoparticles, J. Mater. *Res.* 17, 1356-1362, (2002).
43. W. J. Stark, S. E. Pratsinis, Metal delivery for nanoparticle production, applied as PCT (internationally), May 20, 2003

The invention claimed is:

1. A metal salt consisting of a cationic metal and an anionic group,
    wherein the cationic metal is any metal cation,
    wherein the anionic group is selected from the group consisting of phosphates, borates, silicates, sulfates, carbonates, hydroxides, fluorides and mixtures thereof,
    wherein the metal salt is obtained by
        (a) forming a mixture of at least the metal source of the cationic metal which is a metal carboxylate with a mean carbon number per carboxylate group of at least 3 and at least one anionic source of the anion group into droplets, and
        (b) oxidizing said droplets in a high temperature environment in a range of 1200 to 2600° C.,
    wherein the metal salt releases less than 5 wt % water upon heating to 900° C. at a heating rate of 10° C. per minute; and
    wherein the BET equivalent diameter is in the range of 5 to 200 nm.
2. The metal salt of claim 1, that releases more than 90 wt % of all water upon heating to 500° C. at a heating rate of 10° C. per minute.
3. The metal salt of claim 1 that has percolating phases.
4. The metal salt of claim 1 that is a biomaterial.
5. The metal salt of claim 1, which is a tricalcium phosphate.
6. The metal salt of claim 1, which is an alpha-tricalcium phosphate with a specific surface area (measured by nitrogen adsorption at 196° C. according to the BET-method) of more than 3 m$^2$/g, or a beta-tricalcium phosphate with a specific surface area (measured by nitrogen adsorption at 196° C. according to the BET-method) of more than 1 m$^2$/g.
7. A bone cement comprising the metal salt of claim 1.
8. A resorbable material for implants for medical application comprising the metal salt of claim 1.
9. A toothpaste containing, as at least one of a fluoride source and an abrasive aid, the metal salt of claim 1.
10. A foodstuff containing, as a fluoride source, the metal salt of claim 1.
11. A catalyst support for medical application comprising the metal salt of claim 1.
12. A molecular sieve for medical application comprising the metal salt of claim 1.
13. A polymer for medical application containing, as a filler, the metal salt of claim 1.
14. A biodegradable or bioresorbable material for medical application containing, as at least one of a UV stabilizer and a degradation activator, the metal salt of claim 1.
15. The metal salt of claim 1, which is amorphous.

* * * * *